United States Patent
Den Boef

(10) Patent No.: US 9,222,834 B2
(45) Date of Patent: Dec. 29, 2015

(54) INSPECTION APPARATUS AND METHOD

(71) Applicant: ASML Netherlands B.V., Veldhoven (NL)

(72) Inventor: Arie Jeffrey Den Boef, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 83 days.

(21) Appl. No.: 13/767,769

(22) Filed: Feb. 14, 2013

(65) Prior Publication Data

US 2013/0215404 A1 Aug. 22, 2013

Related U.S. Application Data

(60) Provisional application No. 61/601,156, filed on Feb. 21, 2012.

(51) Int. Cl.
*G01J 3/44* (2006.01)
*G03F 7/20* (2006.01)
(Continued)

(52) U.S. Cl.
CPC .............. *G01J 3/4412* (2013.01); *G01J 3/44* (2013.01); *G01N 21/956* (2013.01);
(Continued)

(58) Field of Classification Search
CPC ............ G01N 21/9501; G01N 21/956; G01N 21/4788; G03F 7/70625
USPC ...................... 356/237.1–241.6, 242.1–243.8, 356/426–431, 600–640
See application file for complete search history.

(56) References Cited

U.S. PATENT DOCUMENTS 3,573,353 A * 4/1971 Henriques et al. ............ 386/313
3,614,235 A * 10/1971 Munnerlyn .................... 356/514
(Continued)

FOREIGN PATENT DOCUMENTS

EP 1 628 164 A2 2/2006
JP 2002-543381 A 12/2002
(Continued)

OTHER PUBLICATIONS

Ausschnitt, C.P., "A New Approach to Pattern Metrology," Proceedings of SPIE—Metrology, Inspection, and Process Control for Microlithography XVIII, vol. 5375, 2004; pp. 51-65.
(Continued)

*Primary Examiner* — Gregory J Toatley
*Assistant Examiner* — Jarreas C Underwood
(74) *Attorney, Agent, or Firm* — Sterne, Kessler, Goldstein & Fox P.L.L.C.

(57) ABSTRACT

A spectroscopic scatterometer detects both zero order and higher order radiation diffracted from an illuminated spot on a target grating. The apparatus forms and detects a spectrum of zero order (reflected) radiation, and separately forms and detects a spectrum of the higher order diffracted radiation. Each spectrum is formed using a symmetrical phase grating, so as to form and detect a symmetrical pair of spectra. The pair of spectra can be averaged to obtain a single spectrum with reduced focus sensitivity. Comparing the two spectra can yield information for improving height measurements in a subsequent lithographic step. The target grating is oriented obliquely so that the zero order and higher order radiation emanate from the spot in different planes. Two scatterometers can operate simultaneously, illuminating the target from different oblique directions. A radial transmission filter reduces sidelobes in the spot and reduces product crosstalk.

12 Claims, 11 Drawing Sheets

(51) Int. Cl.
*G03F 9/00* (2006.01)
*G01N 21/956* (2006.01)
*G01N 21/47* (2006.01)
*G01N 21/95* (2006.01)

(52) U.S. Cl.
CPC ....... *G03F 7/70625* (2013.01); *G03F 7/70633* (2013.01); *G03F 9/7026* (2013.01); *G01N 21/4788* (2013.01); *G01N 21/9501* (2013.01); *G01N 21/95607* (2013.01)

(56) References Cited

U.S. PATENT DOCUMENTS

| | | | |
|---|---|---|---|
| 4,410,278 A * | 10/1983 | Makihira et al. | 356/445 |
| 4,650,321 A * | 3/1987 | Thompson | 356/73 |
| 4,989,189 A * | 1/1991 | Sander et al. | 369/13.29 |
| 5,337,146 A * | 8/1994 | Azzam | 356/367 |
| 5,486,701 A | 1/1996 | Norton et al. | |
| 5,493,555 A * | 2/1996 | Kimura et al. | 369/110.03 |
| 5,859,424 A * | 1/1999 | Norton et al. | 250/226 |
| 6,184,984 B1 | 2/2001 | Lee et al. | |
| 6,201,601 B1 * | 3/2001 | Vaez-Iravani et al. | 356/237.4 |
| 6,483,580 B1 * | 11/2002 | Xu et al. | 356/300 |
| 6,657,736 B1 * | 12/2003 | Finarov et al. | 356/625 |
| 6,919,957 B2 * | 7/2005 | Nikoonahad et al. | 356/237.2 |
| 7,076,024 B2 | 7/2006 | Yokhin | |
| 7,161,672 B2 * | 1/2007 | Gornushkin et al. | 356/328 |
| 7,173,699 B2 * | 2/2007 | Xu et al. | 356/369 |
| 7,227,637 B2 | 6/2007 | Wang et al. | |
| 7,292,341 B2 * | 11/2007 | Brill et al. | 356/445 |
| 7,315,384 B2 | 1/2008 | Den Boef et al. | |
| 7,408,646 B2 * | 8/2008 | Rau et al. | 356/445 |
| 7,433,056 B1 * | 10/2008 | Janik | 356/601 |
| 7,463,369 B2 | 12/2008 | Wack et al. | |
| 7,477,405 B2 * | 1/2009 | Finarov et al. | 356/625 |
| 7,483,133 B2 * | 1/2009 | Bareket et al. | 356/326 |
| 7,859,659 B2 * | 12/2010 | Xu et al. | 356/300 |
| 7,929,139 B2 | 4/2011 | Horie et al. | |
| 8,035,824 B2 | 10/2011 | Ausschnitt | |
| 8,040,511 B1 | 10/2011 | Krishnan et al. | |
| 2006/0066844 A1 | 3/2006 | Moribe et al. | |
| 2008/0129986 A1 | 6/2008 | Walsh | |
| 2009/0195768 A1 | 8/2009 | Bijnen et al. | |
| 2010/0053627 A1 * | 3/2010 | Shyu et al. | 356/446 |
| 2011/0194092 A1 | 8/2011 | Smilde et al. | |

FOREIGN PATENT DOCUMENTS

| | | |
|---|---|---|
| JP | 2009-058259 A | 3/2009 |
| WO | WO 2012/095808 A1 | 7/2012 |

OTHER PUBLICATIONS

Ausschnitt, C.P, "Wafer-to-wafer control using on-demand pattern metrology," Solid State Technology, published Jan. 1, 2005; 7 pages.

Wikipedia.org, "Apodization," accessed at http://en.wikipedia.org/wiki/Apodization, accessed on Jan. 22, 2013; 2 pages.

Wikipedia.org, "Optical transfer function," accessed at http://en.wikipedia.org/wiki/Optical_transfer_function, accessed on Jan. 24, 2013; 4 pages.

Wikipedia.org, "Window function," redirected from Apodization function, accessed at http://en.wikipedia.org/wiki/Apodization_function, accessed on Jan. 22, 2013; 13 pages.

Kubacki, E., "Perplexed by Polarizers? A practical look at polarizers reveals their suitability for various applications," Photonics Spectra, Dec. 2006; 4 pages.

Wikipedia.org, "Rochon prism," accessed at http://www.en.wikipedia.org/wiki/Rochon_prism, accessed on Dec. 1, 2012; 1 page.

International Search Report directed to related International Patent Application No. PCT/EP2013/051878, mailed May 15, 2014; 3 pages.

* cited by examiner

Fig. 16(a)
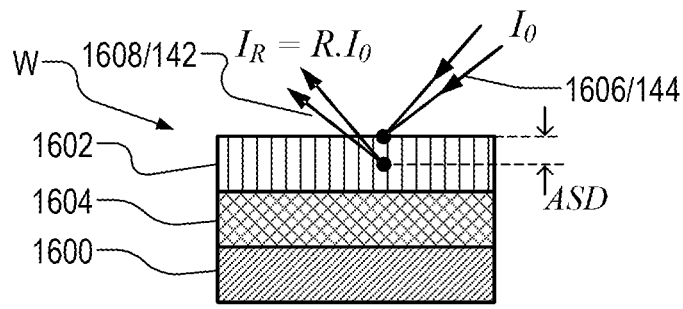
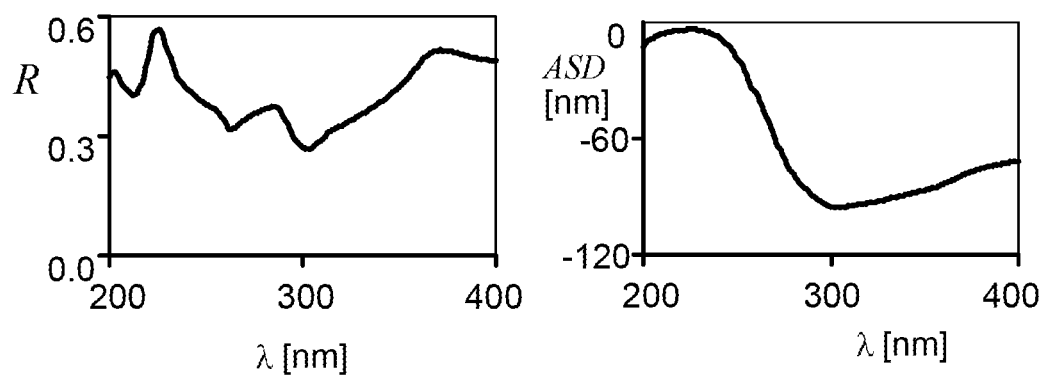
Fig. 16(b)   Fig. 16(c)
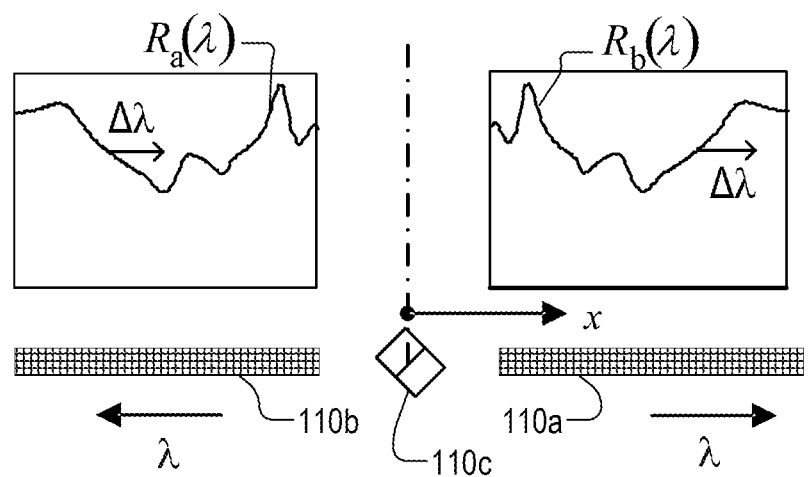
Fig. 17

INSPECTION APPARATUS AND METHOD

FIELD

The present invention relates to apparatus and methods of inspection usable, for example, in the manufacture of devices by lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Spectroscopic scatterometry has the benefit of the hardware is relatively simple, which helps to improve matching and calibration. However, it has difficulties measuring very isolated features, and asymmetry of the metrology gratings. Angle-resolved scatterometry is optically more complicated, which complicates calibration and matching. Moreover, in practice, multiple adjustable wavelengths are needed, which leads to complex and expensive optics. As the resolution of lithographic processes increases, ever smaller features are created on substrates. In order to perform scatterometry at the resolution of the smallest features, it may be desirable to use shorter wavelengths of radiation, comparable to those used in the lithographic process itself. Wavelengths in the ultraviolet (UV) range may be effective for this in principle. However, optical systems for such wavelengths become particularly complex.

There is accordingly a desire for new forms of scatterometer, particularly ones suitable for measuring metrology targets with feature sizes at the resolution of current and next-generation lithographic processes. The inventor has recognized that a limitation of known spectroscopic scatterometers is that they make no use of higher diffracted radiation from the target grating.

A new form of scatterometer has been proposed in the paper "A New Approach to Pattern Metrology" Christopher P. Ausschnitt, published in Metrology, Inspection, and Process Control for Microlithography XVIII, edited by Richard M. Silver, Proceedings of SPIE Vol. 5375 (SPIE, Bellingham, Wash., 2004), DOI: 10.1117/12.539143. Unlike conventional spectroscopic scatterometers, Ausschnitt's so-called MOXIE system uses both zero order and first order diffracted radiation. It also uses a target grating on the substrate itself to resolve the diffracted orders into a spectroscopic signal. However, this system is also not optimized for measuring pattern asymmetries. Moreover, the spectral resolution of the first order signal is dependent on the target geometry and is expected to be too small for practical metrology applications.

Another problem in known scatterometry techniques is the space or "real estate" occupied by scatterometry targets on product substrates. Targets must be kept away from one another and from product features, to avoid cross-talk between measurements. The inventor has further recognized that one cause of cross-talk is that an illumination spot of the instrument has a point spread function with significant sidelobes of energy around a main spot.

A problem in lithographic processes generally is that height measurements used for controlling the transfer of a pattern to a substrate may be influenced unpredictably by process-dependent influences.

SUMMARY

According to first aspect of the present invention, there is provided inspection apparatus comprising a spectroscopic scatterometer having illumination optics for directing broadband radiation with an angle of incidence at a spot on a target structure, the target structure in use comprising a periodic grating, zero order detection optics for receiving radiation reflected from the target and for forming and detecting a spectrum of the reflected radiation, and higher order detection optics for receiving radiation diffracted at one or more higher orders by the periodic grating in the target structure, and for forming and detecting a spectrum of the received diffracted radiation.

In one embodiment, the illumination optics and zero order detection optics process radiation generally in a first plane perpendicular to a plane the target structure, while the higher order detection optics are arranged to process radiation in a second plane, angled relative to the first plane, the higher order diffracted radiation entering the second plane during use of the apparatus as a result of an oblique orientation of lines the periodic grating in the target structure, relative to the first plane.

Putting the higher order radiation into a different plane facilitates the practical layout of such an instrument. In one embodiment the first plane is set at an angle of 45° relative to the expected orientation of the lines in the periodic grating, and a second spectroscopic scatterometer is provided for simultaneous measurement of the same target structure, a first plane of the second spectroscopic scatterometer being arranged at right angles to the first plane of the first-mentioned spectroscopic scatterometer. Optical components can be shared between the higher order detection optics of the first-mentioned and second scatterometers.

The present invention in the first aspect further provides a method of measuring properties of a target structure on a substrate, a target structure including a periodic grating, the method comprising obtaining a zero order spectrum and at least one higher order spectrum from the target structure using an inspection apparatus according to the first aspect of the present invention as set forth above, and processing the measured spectra so as to obtain measurements of one or more parameters of the target structure.

According to a second, independent aspect of the present invention, there is provided a spectroscopic scatterometer having illumination optics for directing broadband radiation with an angle of incidence at a spot on a target structure, detection optics for receiving radiation diffracted at a zero or higher order from the target structure and for forming and detecting a spectrum of the diffracted radiation, wherein the detection optics comprises a symmetric diffraction grating arranged to form a symmetrical pair of spectra of the reflected radiation, and wherein a pair of spectrum detectors are arranged to detect both of the spectra, the apparatus further comprising a processor for combining measurements from both detectors to obtain a single detected spectrum of the reflected radiation.

A spectroscopic scatterometer according to the second aspect of the present invention can have a very simple optical construction compared with known spectroscopic apparatus, suitable for example to use UV radiation.

A spectroscopic scatterometer according to the second aspect of the present invention with a symmetrical pair of spectra can be made to have reduced sensitivity to defocus, compared with a conventional single-spectrum arrangement. In one embodiment, a further detector is arranged to receive a zero order beam of the diffraction grating, the further detector being located at a point generally in between the pair of spectrum detectors, and signals from the further detector are used for monitoring focus of the spot on the target structure.

A spectroscopic scatterometer according to the second aspect of the present invention may be used to form the zero order and/or the higher order detection optics in an apparatus according to the first aspect of the present invention. Examples further below will illustrate this with reference to the drawings.

The present invention in the second aspect further provides a method of measuring properties of a target structure on a substrate, a target structure including a periodic grating, the method comprising obtaining a spectrum from the target structure using an inspection apparatus according to the second aspect of the present invention as set forth above, and processing the detected spectrum so as to obtain measurements of one or more parameters of the target structure.

The invention in a third aspect provides an optical apparatus including illumination optics for focusing a beam of radiation at a spot on a target structure, wherein a filter is provided for imposing on the beam (prior to focusing) a transmission loss increasing with radial distance from an optical axis of the beam, thereby reducing energy in sidelobes in a point spread function of the illumination optics.

The optical apparatus including the illumination optics may be a scatterometer according to the first or second aspect of the invention for example. The suppression of sidelobes in the point spread function can reduce cross-talk between neighboring features, for example to allow more accurate measurements of target properties, and/or the use of smaller targets closer to neighboring structures.

The invention in the third aspect further provides a method of measuring properties of a target structure on a substrate, the method comprising illuminating the target structure with a spot of radiation using an optical apparatus according to the third aspect of the invention as set forth above, detecting radiation diffracted by the target structure and processing the detected radiation to obtain measurements of one or more parameters of the target structure.

The inventor has recognized that a spectroscopic scatterometer having the symmetrical pair of spectra (similar to that used the second aspect of the invention described above) can alternatively or in addition be used to obtain information of process-dependent variations influencing height measurements made for control of a lithographic patterning process. These influences, which may vary from substrate-to-substrate and lot-to-lot, may cause a height sensor to report a different height than the true surface height. This height error may be referred to as an apparent surface depression (ASD), and causes inaccuracy in a subsequent lithographic step that uses height measurements for example to focus an optical projection system.

According to a fourth, independent aspect of the present invention, there is provided a spectroscopic scatterometer having illumination optics for directing broadband radiation with an angle of incidence at a spot on a target structure, detection optics for receiving radiation diffracted at a zero or higher order from the target structure and for forming and detecting a spectrum of the diffracted radiation, wherein the detection optics comprises a symmetric diffraction grating arranged to form a symmetrical pair of spectra of the reflected radiation, and wherein a pair of spectrum detectors are arranged to detect both of the spectra, the apparatus further comprising a processor for comparing measurements from both detectors to obtain information of an apparent surface depression at the location of the target structure on a substrate.

The invention in the fourth aspect further provides a method of controlling a lithographic apparatus wherein a pattern is applied to a substrate based on height measurements made by the apparatus at one or more locations across a substrate, and wherein a correction is applied to the height measurements based on information of an apparent surface depression obtained using a spectroscopic scatterometer according to the third aspect of the invention, set forth above.

The various aspects of the invention set forth above can be used independently of one another, or two or more aspects may be combined together in the same apparatus or method.

Further features and advantages of the present invention, as well as the structure and operation of various embodiments of the present invention, are described in detail below with reference to the accompanying drawings. It is noted that the present invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

The accompanying drawings, which are incorporated herein and form part of the specification, illustrate exemplary embodiments of the present invention and, together with the description, further serve to explain the principles of the present invention and to enable a person skilled in the relevant art(s) to make and use the present invention.

FIGS. 16(a) to 16(c) illustrate the phenomenon of apparent surface depression affecting height measurements used for example in a lithographic process.

FIG. 17 illustrates a method of obtaining information on apparent surface depression using a scatterometer of the type illustrated in FIGS. 4 and 5, in accordance with the fourth aspect of the invention.

Figure 1:
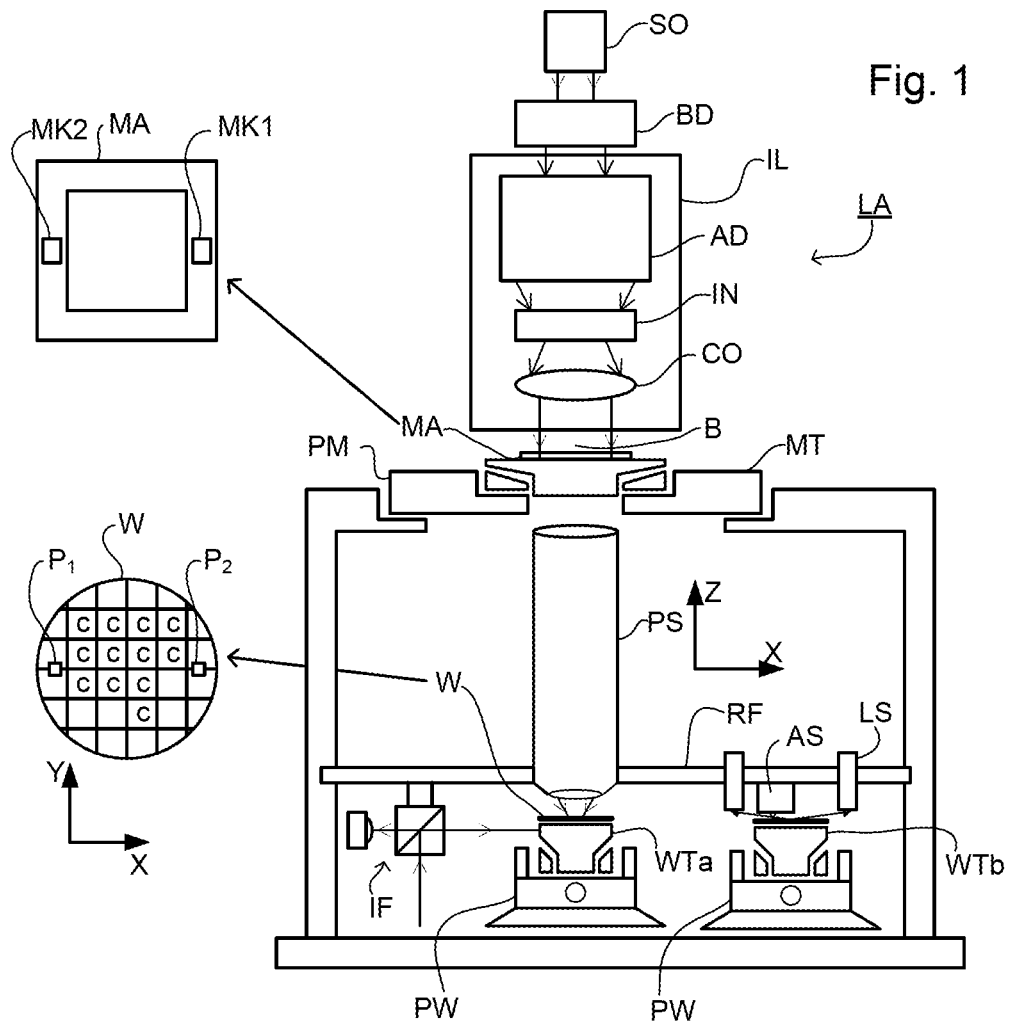
FIG. 1 depicts a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION OF EXEMPLARY EMBODIMENTS

This specification discloses one or more embodiments that incorporate the features of this present invention. The disclosed embodiment(s) merely exemplify the present invention. The scope of the present invention is not limited to the disclosed embodiment(s). The present invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically shows a lithographic apparatus LAP including a source collector module SO according to an embodiment of the present invention. The apparatus comprises: an illumination system (illuminator) IL configured to condition a radiation beam B (e.g., EUV radiation); a support structure (e.g., a mask table) MT constructed to support a patterning device (e.g., a mask or a reticle) MA and connected to a first positioner PM configured to accurately position the patterning device; a substrate table (e.g., a wafer table) WT constructed to hold a substrate (e.g., a resist-coated wafer) W and connected to a second positioner PW configured to accurately position the substrate; and a projection system (e.g., a reflective projection system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks MK1, MK2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
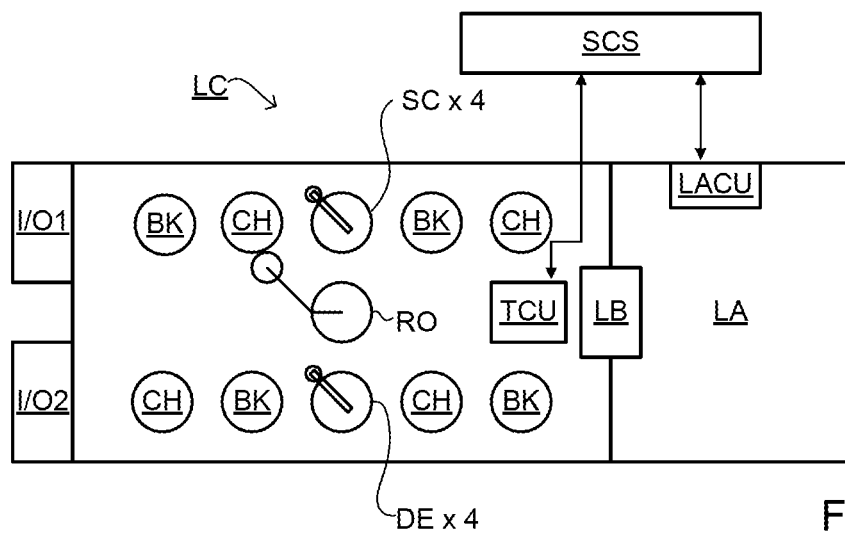
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
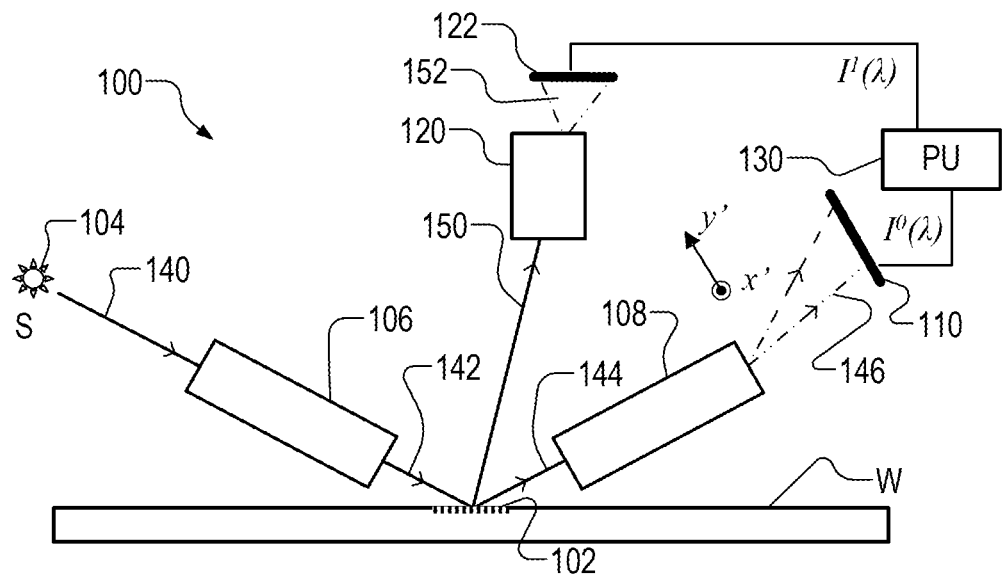
FIG. 3 is a schematic block diagram of a novel inspection apparatus embodying a first aspect of the present invention.

FIG. 3 depicts a novel spectroscopic scatterometer 100 which processes both zero order and higher order radiation, diffracted by a target 102 on substrate W. The apparatus comprises a source 104 of broadband radiation, illumination optics 106 zero order detection optics 108 and detector 110. The scatterometer further comprises first order detection optics 120 and detector 122.

Such a scatterometer may be configured as a normal-incidence scatterometer or an oblique-incidence scatterometer. In the layout illustrated in FIG. 3 and the subsequent diagrams, oblique incidence is used. A particular advantage of such a layout is that reflective optics may be used for the illumination optics 106 and the detection optics 108, 120, simplifying the optical design when the radiation from source 104 is in the deep UV (DUV) and vacuum UV (VUV) waveband. Thus a narrow beam of radiation 140 received from source 104 is formed into a narrow, focused beam 142 to impinge on target 102. Zero order or specular reflected radiation 144 is received by zero order detection optics 108 and split into a spectrum 146. First order radiation 150, diffracted by periodic features within the target 102, is received by first order detection optics 120 and split into a spectrum 152. Spectra of zero order and higher order diffracted radiation are captured by the detectors 110 and 122 respectively, and supplied to processing unit 130. Each detected spectrum records intensity I as a function of wavelength $\lambda$. The zero order spectrum is represented by a function $I^0(\lambda)$, while a first order spectrum is represented by a function $I^1(\lambda)$. In this illustration, only the first order radiation is captured as an example of a higher order. In other embodiments, second, third etc orders may also be captured. In the following description, the first order diffracted radiation will be referred to for simplicity, on the understanding that this is merely one example of higher order diffracted radiation.

From the data received from detectors 110 and 122, the structure or profile giving rise to the detected spectrum may be reconstructed by processing unit 130. The target 102 on substrate W may be a 1-D grating, which is printed such that after development, the bars are formed of solid resist lines. The target 102 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit 130, from knowledge of the printing step and/or other scatterometry processes.

As described above, the target is on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In other words, target shape information is obtained for CD (critical dimension) uniformity and overlay metrology. Overlay metrology is a measuring system in which the overlay of two targets is measured in order to determine whether two layers on a substrate are aligned or not. CD uniformity is simply a measurement of the uniformity of various gratings across the substrate to determine how the exposure system of the lithographic apparatus is functioning. Specifically, CD, or critical dimension, is the width of the object that is "written" on the substrate and is the limit at which a lithographic apparatus is physically able to write on a substrate.

Using the scatterometers described above in combination with modeling of a target such as the target 102 and its diffraction properties, measurement of the shape and other parameters of the structure can be performed in a number of ways. In a first type of process (model-based reconstruction), a diffraction pattern based on a first estimate of the target shape (a first candidate structure) is calculated and compared with the observed diffraction pattern. Parameters of the model are then varied systematically and the diffraction re-calculated in a series of iterations, to generate new candidate structures and so arrive at a best fit. In a second type of process, diffraction spectra for many different candidate structures are calculated in advance to create a 'library' of diffraction spectra. Then the diffraction pattern observed from the measurement target is compared with the library of calculated spectra to find a best fit. Both of these reconstruction methods are in principle known to the skilled reader from using other types of scatterometer. The skilled reader will be able readily to adapt the reconstruction methods to use spectra obtained by the novel instrument disclosed herein. Both model-based and library-based methods can be used together. For example, a coarse fit can be obtained from a library, followed by an iterative process to find a best fit. Examples of techniques for performing model-based reconstruction are Rigorous Coupled Wave Analysis and non-linear regression. In general, for the reconstruction the general form of the structure is known and some parameters are assumed from knowledge of the process by which the structure was made, leaving only a few parameters of the structure to be determined from the scatterometry data.

By capturing higher diffraction orders such as the first order diffracted radiation, the novel spectroscopic scatterometer of FIG. 3, additional parameters for constraining the model or enhancing the library can be used, improving the quality of metrology. The detectors may separately measure the intensity of transverse magnetic- and transverse electric-polarized light and/or the phase difference between the transverse magnetic- and transverse electric-polarized light.

Figure 4:
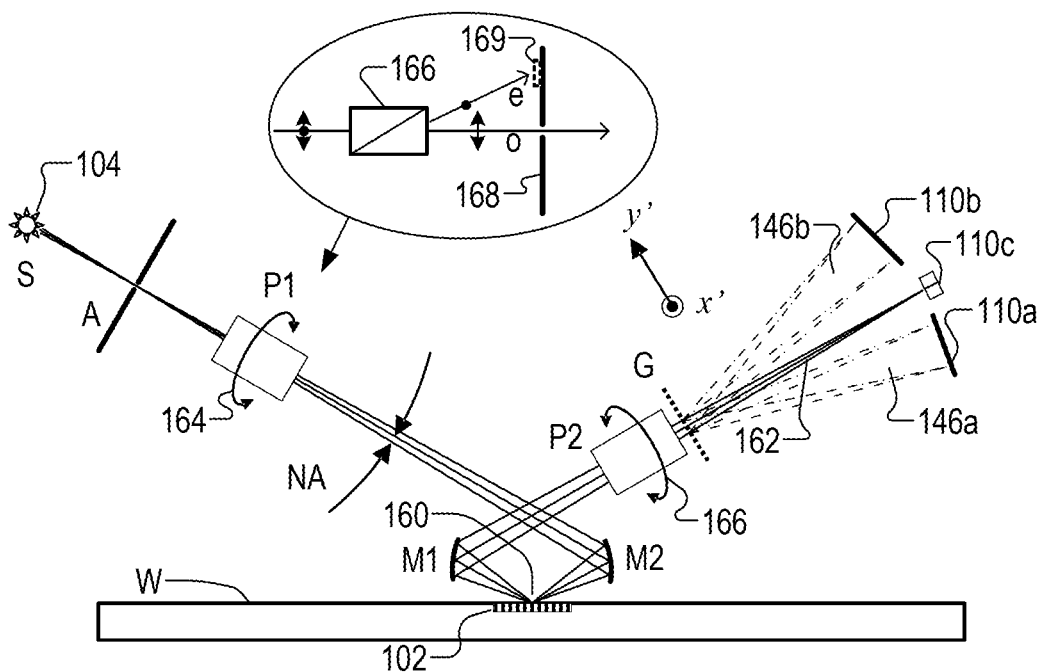
FIG. 4 is a schematic block diagram of a zero order branch in the apparatus of FIG. 3, embodying a second aspect of the present invention, with inset detail of a Rochon prism polarizer.

FIG. 4 shows schematically the illumination optics 106 and zero order detection optics 108 in a little more detail. The source 104 is labeled S, and comprises for example a deuterium gas discharge source producing a broad spectrum of DUV radiation. Such sources are available for example from Hamamatsu Photonics of Japan. Other types of source may be used if preferred, for example laser driven light sources (LDLS) available from a company Energetiq. An aperture plate labeled A defines an entrance aperture to the illumination optics. The aperture may be for example 100×200 µm and elliptical in shape. A polarizer P1 selects one polarization of light from the beam 140 and passes it to a focusing mirror M1 which focuses the polarized beam into a spot 164 illuminating target 102. The illumination optics formed by mirror M1 forms a demagnified image of the aperture A, so that a small spot of diameter for example 20 µm is formed on the target. Because of the oblique angle of incidence, the elliptical spot defined by aperture A is transformed into a substantially circular spot on the target.

Specular reflection of the focused illumination spot 160 is the zero order reflected beam 144, which is captured by a second focusing mirror M2 forming part of the detection optics 108. Detector 110 is shown in a particular form having first and second pixel array detectors 110a and 110b and a central focus detector 110c. Mirror M2 is arranged to focus an image of spot 160 onto detector 110 that the location of focus sensor 110c. Also within the detection optics are a second polarizer P2 and a diffraction grating G. Polarizer P2 serves as an analyzer to block radiation having an unwanted polarization. Diffraction grating G is in this example a simple transmissive phase grating, rather than a conventional spectroscopy grating. Whereas a conventional spectroscopy grating would be designed with features such as "blazing" so as to concentrate as much radiation as possible into a first order spectrum, the relatively simple phase grating used in this system produces a pair of symmetrically-arranged first order spectra of the zero order beam 144. These spectra are labeled 146a and 146b in FIG. 4, and are captured by pixel array detectors 110a and 110b respectively. A portion 162 of zero order radiation 144 passes directly through grating G to form an image of spot 160 on focus detector 110c. Assuming the detection optics has a magnification similar to the demagnification of the illumination optics, the spot diameter on the focus sensor may be of a similar size to the aperture A. Compared with the large NA (numerical aperture) of the known angle resolved scatterometer, the NA of the illumination optics and detection optics is significantly smaller and of the order of 0.1.

As shown by arrows 164 and 166, polarizers P1 and P2 can be rotated to select any desired polarization. Different polarizations can be used for different measurements, as mentioned above, enhancing the amount of data available for analysis. A particular form of polarizer useful in the present apparatus is a Rochon prism, as shown at 166 in the inset detail. A Rochon prism is formed by two pieces of birefringent material. For the wavelengths discussed in this example, a magnesium fluoride crystal is a suitable. As shown in the inset detail, a ray coming in from the left which is unpolarized is separated into its ordinary ray and extraordinary ray components. Specifically, the ordinary ray (o) which is polarized in the plane of the inset diagram passes straight through the prism without deflection, while the extraordinary ray (e), having a polarization into the page is deflected. Only the ordinary ray progresses through the optical system. The extraordinary ray may be actively blocked, if desired, by a stop 168. The extraordinary ray can optionally be detected by a detector (169, shown dotted). This could be useful for example as a way to monitor variations in intensity of the optical signals without stealing any of the wanted radiation.

The analyzing polarizer P2 can also be formed conveniently by a Rochon prism. The length of the Rochon prism in the optical path may be, for example 20 to 30 mm.

In order to avoid confusion of terminology, it is useful to remember that both the target 102 and the grating G are periodic structures acting as diffraction gratings. Thus, the beam entering the zero order detection optics illustrated at the right-hand side of FIG. 4 is the zero order beam, reflected by target 102. Within the detection optics itself, grating G forms part of a spectrometer, and the spectra 146a and 146b comprise first order diffracted radiation of the differential diffraction grating G, while beam 162 impinging on focus detector 110c is the zero order beam of the diffraction grating G.

In addition to having a very simple optical system, favorable to the very short wavelength radiation in the UV region, producing the two spectra and focus beam 162 in the manner illustrated brings advantages to the new design of spectroscopic scatterometer, as will be discussed below. These advantages are independent of the benefits brought by processing higher order radiation diffracted by target 102 (not shown in FIG. 4). A first benefit is that the position of the spot image on focus detector 110c varies according to how well spot 160 is focused on target 102. The focus detector may for example comprise a simple split photodiode. Deviation from ideal focus causes a deviation in the position of the spot on the focus detector, which can be used in a feedback mechanism (not shown) to keep the spot is focused as possible. If desired, properties of the grating G can be tuned so that only a small proportion of the radiation is allowed into this beam for focusing, maximizing the energy in the first order spectra which are of interest for the metrology purpose. An actuator for this focusing mechanism may be arranged for example to move substrate W up and down to restore proper focus. An alternative arrangement of the optical systems will now be described with reference to FIG. 5, in which focusing is further simplified.

Figure 5:
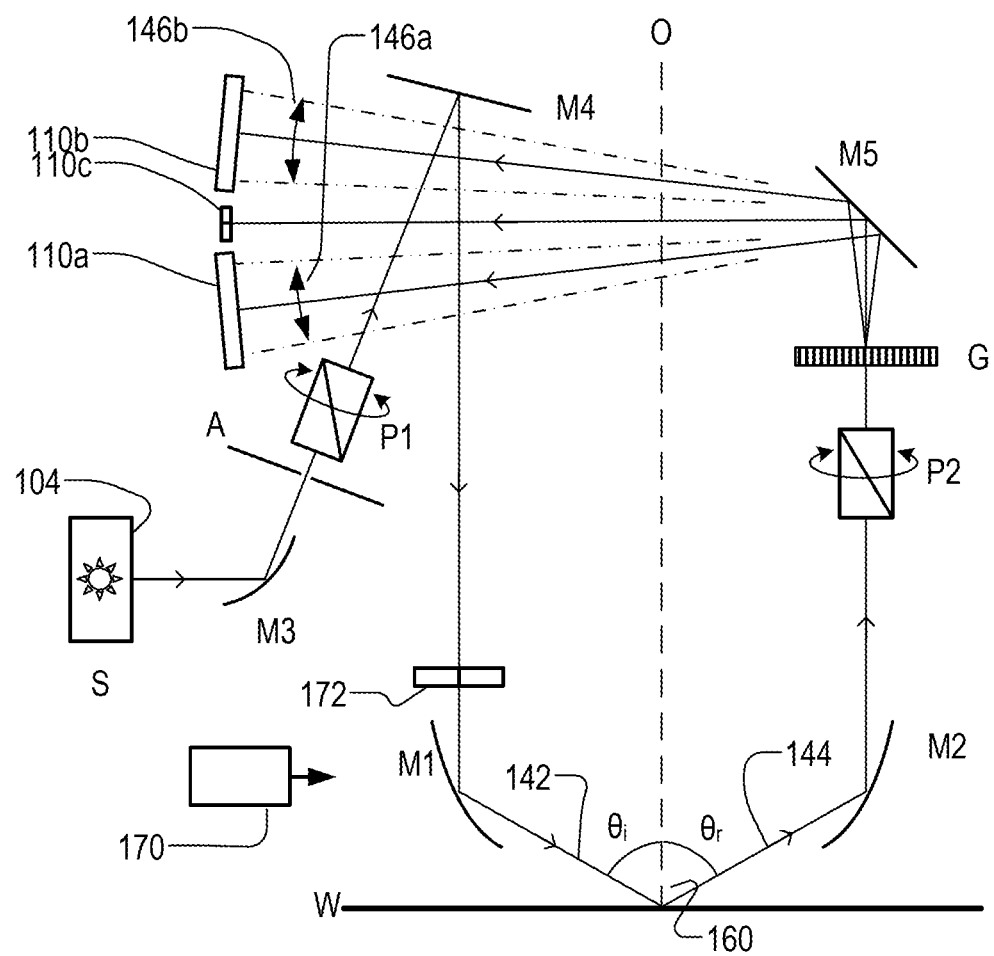
FIG. 5 is a schematic diagram of the zero order branch in a practical embodiment of the apparatus of FIG. 3.

Referring to FIG. 5, a rearranged version of the spectroscopic scatterometer shown in FIG. 4 has essentially the same components in a different layout. Components having the same reference numbers or labels as those in FIG. 4 have substantially the same form and function. Differences may be in the magnification, angle of incidence and so forth. An optical path of the radiation in this modified arrangement is folded so as to provide a more compact and vertically distributed apparatus. Such an arrangement can better fit in and instrument housing, particularly where it is to with place or sit alongside existing metrology systems. In a practical instrument, it may be desirable to have the new scatterometer available for some tasks, while known forms of spectroscopic and/or angle-resolved scatterometer are also provided, for other tasks. Folding of the optical path is achieved by additional mirrors M3, M4, M5 as shown in the diagram. Sections of the optical path between mirror M4 and M1 and between mirror M2 and polarizer P2 are parallel with one another, and normal to the plane of substrate W. By this arrangement, focusing of spot 160 onto the target can be controlled by an actuator 170 which simply moves up and down a subassembly comprising mirrors M1 M2. In this way, the amount of mass to be moved by the focus actuator can be much smaller than if the entire substrate table or the entire optical system of the scatterometer as to be moved to achieve focusing.

Also shown in FIG. 5, and optionally present in FIG. 4 arrangement likewise, is a filter 172 which has a rotationally-symmetric transmission filter with a gradually decreasing transmission in the radial direction. This filter ensures that sidelobes in the point-spread function of the optics are significantly suppressed, resulting in less light "leaking" outside the target area. An example of such a filter suitable for use at DUV wavelengths and its effects on the performance of the scatterometer will be described further below, with reference to FIGS. 14 and 15.

An axis normal to the plane of the substrate is shown and labeled O in the diagram. The angles of incidence and reflection of the zero order beam are labeled $\theta_i$ and $\theta_r$, respectively. The angle of incidence may for example be 60° in a practical embodiment. The angle of reflection is of course equal to the angle of incidence, for the zero order beam. Compared with the two-mirror arrangement of FIG. 4, the arrangement of FIG. 5 is clearly more complicated, and requires additional components. Nevertheless, refractive optical components are avoided, in favor of reflective optics. This has particular benefits for the future generation of instruments, in which the radiation is in the DUV waveband.

Again, the first order diffracted radiation from target 102, and the first order detection optics 120 which are present in each of the described embodiments, are not illustrated in FIG. 5, for simplicity. As will be explained further below, the apparatus in the examples described be configured and used in such a manner that the first order diffracted radiation is deflected out of the plane of the diagram, so that the first order detection optics do not need to share space with the zero order optics.

Figure 6A:
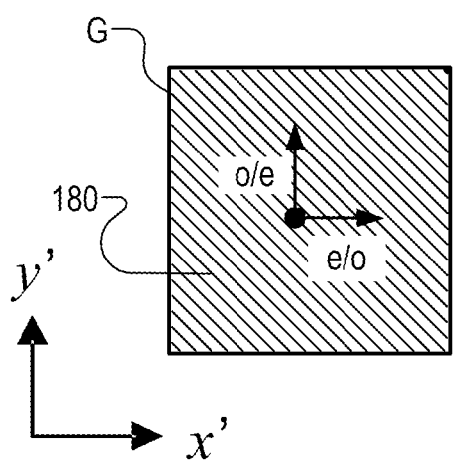
FIGS. 6(a) and 6(b) illustrate features of a spectroscopic grating in the apparatus of FIGS. 3 to 5.
Figure 6B:
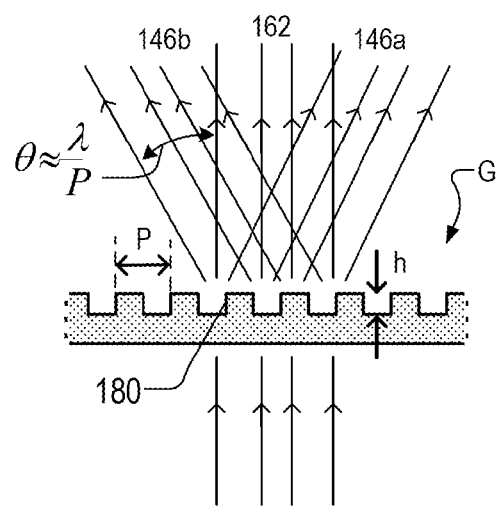
Figure 6C:
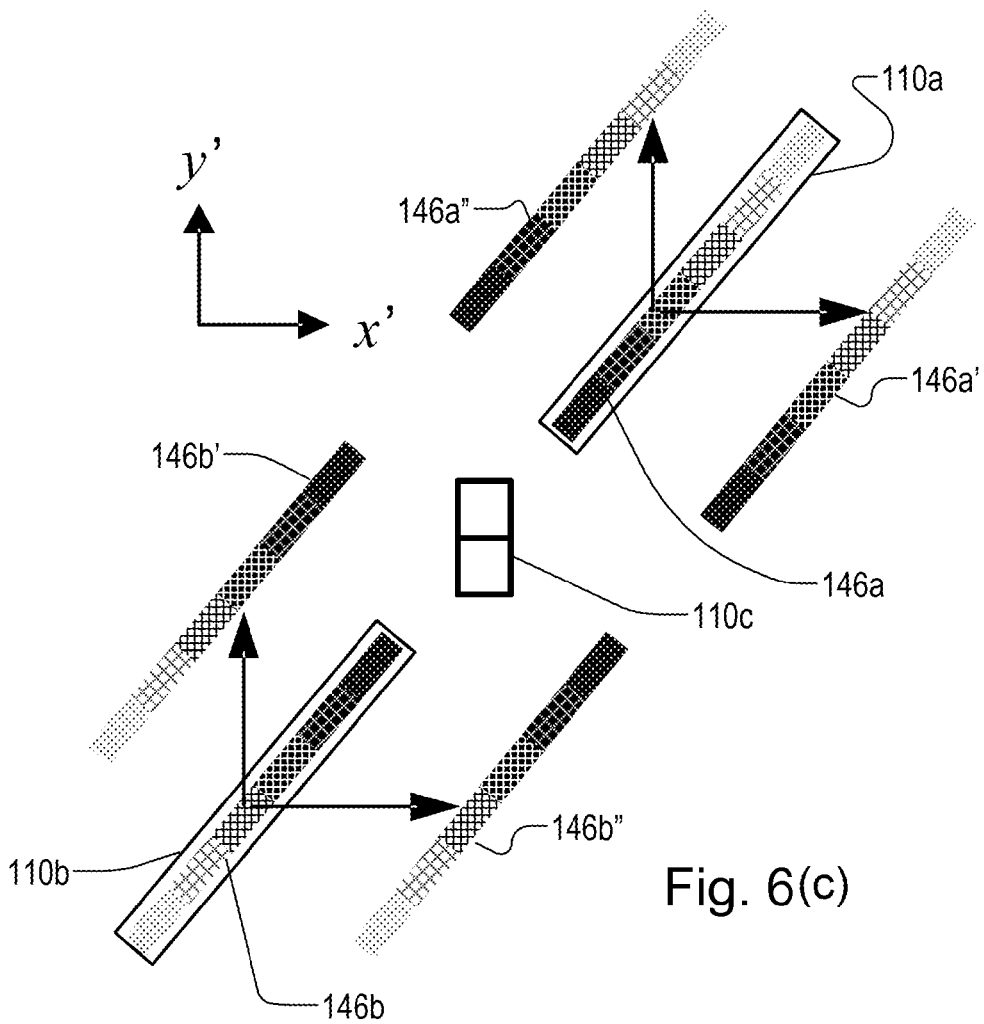
FIG. 6(c) illustrates the displacement of spectra of differently polarized radiation generated by the grating in the apparatus.

FIG. 6 illustrates the form of spectroscopic grating G in embodiments of the present invention, and further illustrates a technique used in the embodiments of FIGS. 4 and 5, to avoid crosstalk between spectra of different polarizations.

FIG. 6(a) is a plan view of phase grating G, with grating lines 180. FIG. 6(a) is a cross-section of the phase grating. The grating in this example is transmissive, and made from a glass or crystal that is transparent to the radiation in use, and has a certain refractive index different from the surrounding medium. Quartz may be used in the present example. Each grating line 180 comprises portions of different thickness, in this case a simple rectangular wave pattern with period or pitch P and height h. Some of the incident radiation (here shown arriving at the back side of the grating) passes straight through the grating to form a zero order beam 162. Other parts of the radiation are diffracted into first order beams 146a, 146b having angles dependent on the pitch P and wavelength λ.

The rays illustrated in FIG. 6(b) are parallel and monochromatic. Where the rays contain radiation of different wavelengths, the different angles of diffraction cause the higher order beams to resolve into spectra. Where the rays are not parallel, some blurring of the spectra can be introduced, as discussed below. The relative strengths of the zero and higher order beams can be adjusted by tuning the height h of the grating. The tuning can in particular be used to accentuate the first orders, say, in a particular section of the wavelength range, and attenuate another section. This facility can be exploited as described below, to compensate at least partially a non-uniform spectral response of the light source and detectors.

Diffraction grating G can in other embodiments be a reflective grating rather than a transmissive one as shown. The reflective grating can take the place of one of the folding mirrors, for example mirror M5 in the example of FIG. 5, or it may be an additional component, with suitable adaptation of the layout. The grating could be formed on a curved mirror, but with a consequent increase in complexity. The gratings in these examples are phase gratings, which have a greater efficiency (lower light loss) than amplitude gratings. Nevertheless, the apparatus would work in the same way with an amplitude grating.

As mentioned already, the analyzing polarizer P2 may comprise a Rochon prism having a form similar to the polarizing prism 166 used for P1. Whereas the radiation leaving prism P1 is of a single, linear polarization, interaction with the target 102 can cause a degree of depolarization, introducing an orthogonal component. In the second prism P2, depending on its orientation, this orthogonal component may be selected for analysis, or the original polarization may be selected. However, according to the function of the Rochon prism P2, both the ordinary and extraordinary components (o-ray and e-ray) emerge from the prism, just in slightly different directions. Therefore without careful design, it is likely that unwanted (e-ray) radiation will strike the grating G and its spectrum could overlap the spectrum of the wanted (o-ray) radiation.

As illustrated in FIG. 6(a), the o-ray may be vertically or horizontally polarized, and the e-ray will be polarized at ninety degrees to that. In order that the spectra detected by detectors 110a and 110b contain only the wanted polarization, the grating G is arranged with its lines 180 at a different angle to the axes of polarization. This angle may be 45 degrees for convenience. The angles through which the rays are spread out to form a spectrum are consequently different to the angle through which the e-ray deviates from the o-ray. As illustrated in FIG. 6(b), the detectors 110a and 110b are similarly oriented at 45 degrees, so as to receive the o-ray spectra 146a and 146b. At the same time, because the e-ray is displaced either vertically or horizontally, with respect to the plane of the diagram, any e-ray spectra 146a', 146b', 146a" or 146b" are displaced out of the line on which the detectors lie.

Figure 7A:
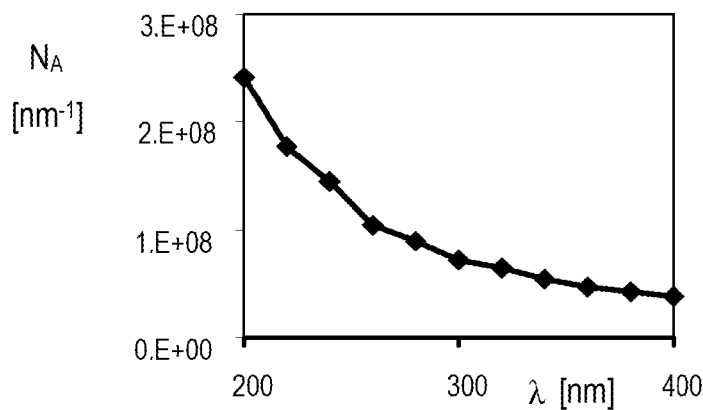
FIGS. 7(a), 7(b) and 7(c) illustrate the management of a photon budget in an example apparatus.
Figure 7B:
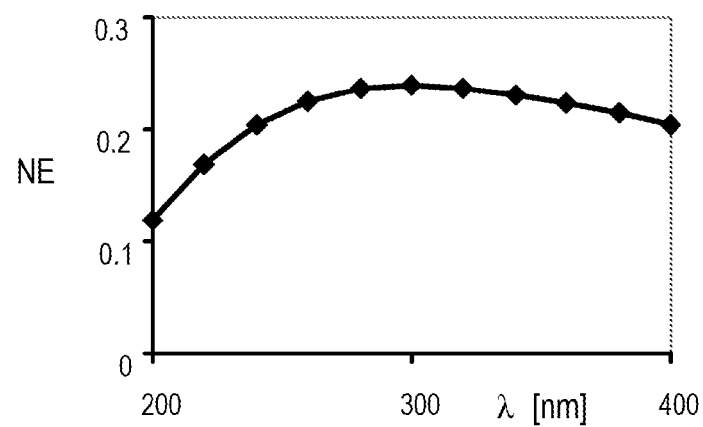

Referring now to FIG. 7, the skilled person understands that an instrument such as a spectroscopic scatterometer can only perform as desired if there is, at the detector, sufficient intensity in the radiation across the spectrum of interest for useful measurements to be made on a reasonable timescale. FIG. 7(a) illustrates the intensity spectrum of a commercially-available deuterium source 104 after the aperture A, converted to a photon count $N_A$ representing the number of photons in a acquisition time. The acquisition time may be, for example, 20 ms in a practical instrument. The source 104 in this example has a a relatively high intensity at shorter wavelengths (200 nm), which falls to a substantially lower level at the longer end of the spectrum (400 nm). FIG. 7(b) illustrates the net efficiency NE of an example illumination and detection optics, from the aperture A to the detector 110. This represents the proportion of the photons that the reach the detector at a given wavelength. This includes, for example, the loss of 50% of the photons at the first polarizer P1, and assumes a certain reflectance at the mirrors M1, M2 etc, as well as a certain efficiency of diffraction grating G. Importantly, the efficiency of the grating can be tailored by design to be more efficient and those wavelengths where the source is weaker, so as to achieve a compensating effect in the shape of the net efficiency spectrum NE. Therefore, as illustrated in this example, the efficiency spectrum can be selected to enhance those wavelengths that are weaker in the source spectrum, relative to those that are stronger.

Figure 7C:
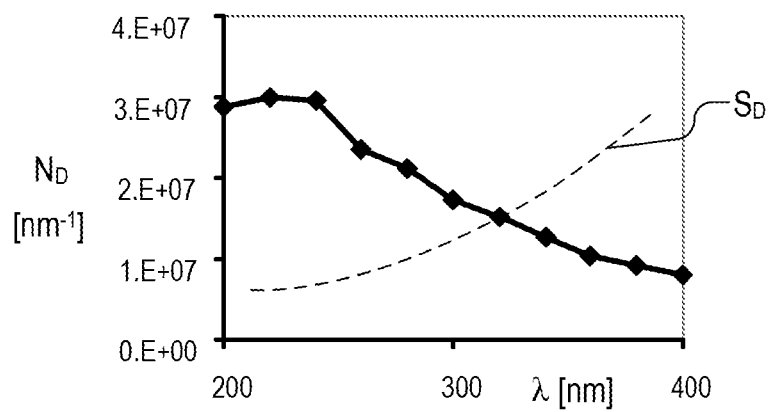
Figure 8:
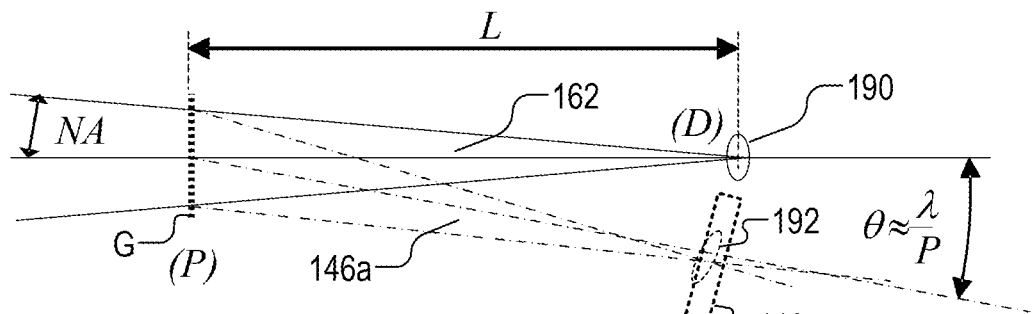
FIGS. 8 and 9 illustrate the management of aberration in a spectrum detected in the apparatus of FIGS. 3 to 5.

FIG. 7(c) illustrates the number $N_D$ of photons at each wavelength at the detector, resulting from the combination of incoming photons and net efficiency through the illumination and detection optics. It will be seen that the number of photons at the detector is still substantially higher at the lower wavelengths than at the longer wavelengths. However, this fall in photon count is matched by a corresponding rise in the sensitivity $S_D$ of detector 110, to achieve a relatively flat response for the instrument as a whole. The response will never be perfectly flat, of course, but can be modeled and/or measured to produce a correction curve to be applied within processing unit 130. FIG. 8 illustrates the phenomena of aberration, that arises in the formation of the spectra 146a and 146b due to the very simple nature of the detection optics. A spot 190 with diameter D is formed on the focus detector from the zero order beam 162 of grating G. A first order spectrum (for example, spectrum 146a) is formed by rays deflected by the action of the grating, which has a period P. The angle θ at which each wavelength λ in the spectrum is deflected depends on both wavelength and grating period, as shown.

Figure 9:
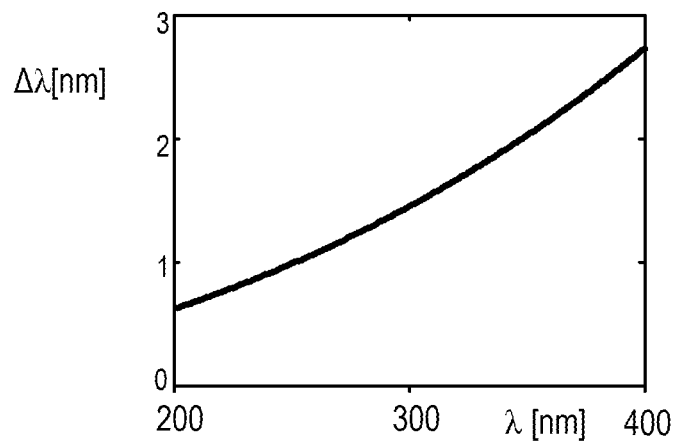

Whereas, in a conventional spectrometer, came be taken to ensure that the rays arriving at the grating were parallel, in this simple optical system, the rays are converging as shown to the spot 190. Consequently, they are not parallel, by an amount dependent on the numerical aperture NA. Consequently, for each wavelength in the diffraction spectrum, the rays do not focus perfectly to a spot, and the spot 192 is rather blurred due to aberrations. Detector 110a is placed at an angle, shown in dotted outline, so as to obtain the best approximation of a focused spectrum. The aberration can be modeled as illustrated in FIG. 9, giving an uncertainty Δλ in the wavelength that will be reported by the spectrometer based on a design with parameters approximately NA=0.01, L=100 mm, D=200 and P=200 μm. This amount of blurring of the spectrum is within acceptable limits for a useful instrument. Moreover, because the cause of the blurring can be very well modeled, the amount of blurring can be calculated so processor 130 can apply deconvolution to the measured spectra, and further improve accuracy.

Figure 10:
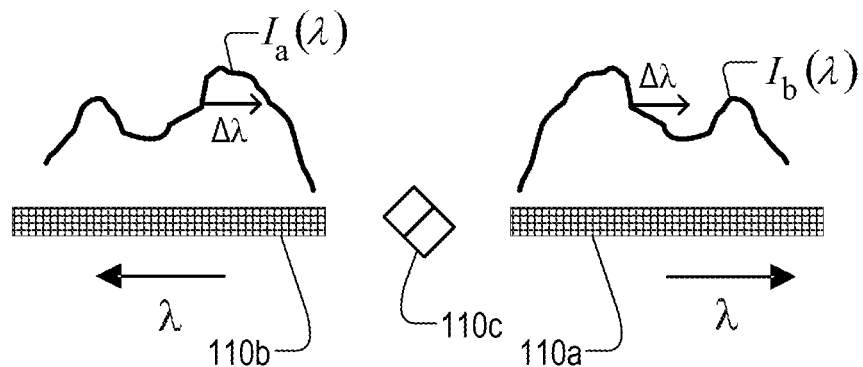
FIG. 10 illustrates the management of focus error in the apparatus of FIGS. 4 and 5.

FIG. 10 illustrates some benefits of the novel arrangement, in which symmetrically opposite spectra are recorded simultaneously on the two detectors 110a and 110b. Each detector may, for example, comprise a CCD array having 1024 pixels by 16 pixels. Each pixel position in the longer direction represents a different point on the spectrum. Intensity is measured by pixels across the shorter direction of the array are integrated into a single value. Example spectra as seen by the detectors are represented by the curves $I_a(\lambda)$ and $I_b(\lambda)$. It will be noticed that the spectra of mirror images of one another, centered on the focus detector 110c, as would be expected. Values from both sensors can be combined (averaged) to obtain a measurement of the intensity of the spectrum at a given wavelength, according to the formula $$I(\lambda)=(I_a(\lambda)+I_b(\lambda))/2$$

An important performance parameter for a spectroscopic scatterometer is the robustness of the reported spectrum against errors caused by offsets in the focus of the spot 160 on the target 102. In general, an error ΔZ in focus will produce an error Δλ(ΔZ) in the accuracy of the reported wavelength. Therefore, in known spectroscopic scatterometers, it is necessary for focus to be very tightly controlled to minimize the offsets. On the other hand, in the symmetrical design used in the present embodiments, focus offsets have much less effect on the reported wavelength. To understand why this is the case, it should be noted that focus offsets will cause a shift Δλ(ΔZ) of both spectra in the same direction, while the reported wavelength varies in opposite directions on the two sensors. Thus, the shift to longer wavelengths in the spectrum reported by detector 110a is compensated by a shift to shorter wavelengths in the detector 110b. Consequently, while defocus leads to a blurring of the reported spectrum, there is no shift in the wavelength direction caused by focus errors. Consequently, performance parameters of the focusing system can be relaxed, leading to a simpler construction and/or faster measurement performance. If desired, because the additional spectral blurring caused by defocus is easily modeled, processor 130 can take this into account using a focus error signal from the focusing system.

In addition to providing a focus error signal, detector 110c can be used to measure variations in the overall intensity of the illumination, so as to correct for such variations before processing the measured spectra. This avoids the need to provide a separate sensor elsewhere in the system.

As a further benefit of the symmetrical design of the spectroscopic scatterometer, information can be obtained on wavelength-dependent variations in the apparent focusing position of the scatterometer (apparent surface depression or ASD). This in turn can be useful to predict process-dependent ASD effects that influence the measurement of substrate height during exposure of a subsequent pattern. An example apparatus and method exploiting this potential will be illustrated and described below with reference to FIGS. 16 and 17.

Figure 11:
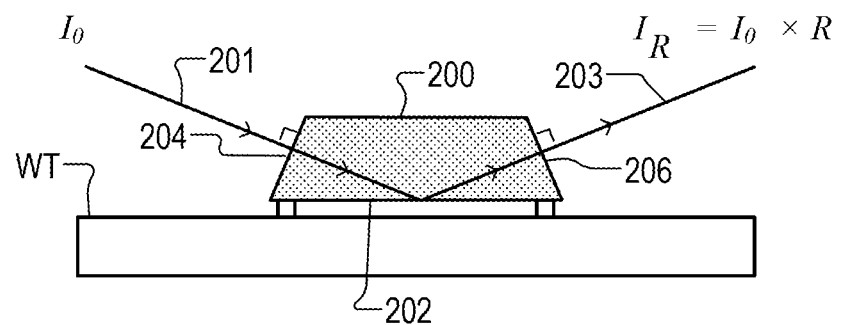
FIG. 11 illustrates a novel calibration prism useful in setting up the apparatus of FIGS. 3 to 5.

FIG. 11 illustrates a simple device 200 useful in the calibration of an instrument such as the spectroscopic scatterometer described above. A particular requirement is for the spectral response of the complete instrument to be measured and stored for correction purposes, before the spectral response of actual targets 102 can be accurately measured and calculated. When moving to shorter wavelengths, such as DUV wavelengths, the availability of reference reflectors becomes a problem. At such wavelengths, conventional reflecting materials exhibit their own wavelength-dependency. Device 200 comprises a prism of a highly transparent material such as quartz or fused silica, that does not exhibit great wavelength dependence in the waveband of interest. The present can be located on the substrate support WT of the instrument, such that an incoming ray 201 is reflected by total internal reflection at a face 202 to give an outgoing ray 203. Entry face 204 and exit face 206 are performed so that they are completely normal to the direction of the incident ray 200 and one or 203, and no deviation occurs. The entry and exit faces can optionally be given a small curvature that matches a convergence or divergence of the incident and reflected beams. In this way the light rays "hit" the faces perpendicularly so the beam distortion that is caused by the faces is minimized.

The intensity $I_R$ of the outgoing ray 203 is related to the intensity $I_0$ of the incoming ray 201 by a reflectance factor R which is known with very high accuracy, and depends only on the refractive index of the material from which the prism is made. The formula for reflectance R is $$R = t^2 a$$

where a is the absorption of the prism material and t is the transmission at each of the faces 204, 206. Provided the refractive index n is well known at each wavelength, the transmission t can be calculated from Fresnel's equation $$t = 4n/(1+n)^2$$

The calibration process whereby spectral response of the complete instrument, which would otherwise be a challenging, is simplified by the use of this accurate reference device. For calibrating an instrument with different angles of incidence, a different prism can be made. Alternatively, a single prism could be made that has facets at different angles, if preferred.

Figure 12:
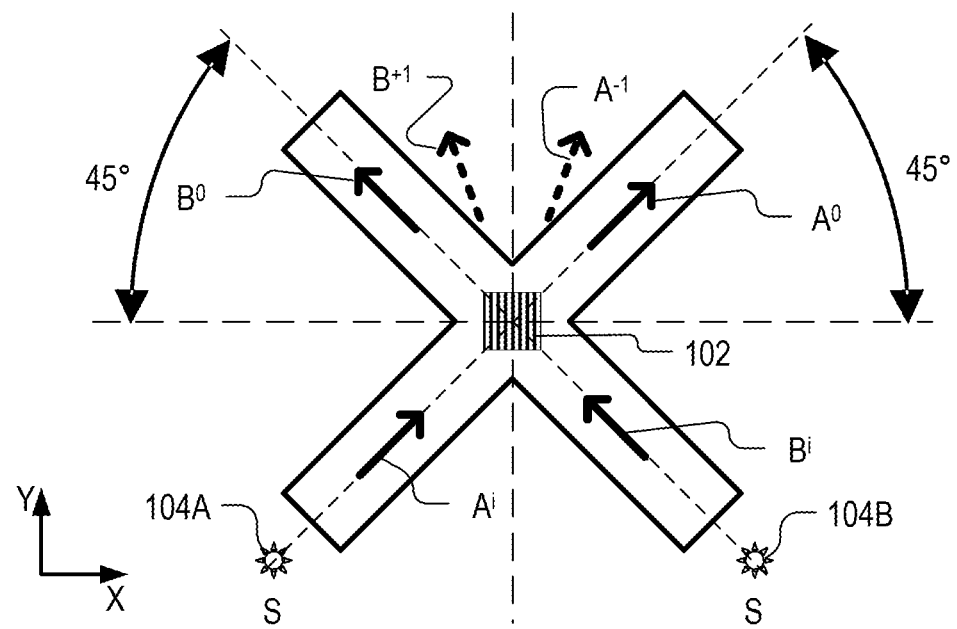
FIG. 12 illustrates the layout of a dual-branch scatterometer including two of the apparatus of FIGS. 3 to 5 in an embodiment with oblique orientation relative to a target grating direction, and showing the general location of first order diffracted radiation in a different plane to the zero order radiation.

FIG. 12 illustrates the layout of a practical apparatus comprising two of the spectroscopic scatterometers of the type shown for example in FIG. 4 or FIG. 5, arranged at right angles to one another Each scatterometer will be referred to as a branch of the complete instrument, and these branches are labeled branch A and a branch B for convenience. Remembering that the target 102 has the form of a diffraction grating in a typical situation, the lines of this grating are shown oriented vertically in the diagram, that is parallel to the Y axis. The scatterometer branches A and B are oriented at right angles to one another such that both are at 45° to both the X and Y axes. Thus the incoming beam of branch A travels schematically from a source SA at bottom left, reflects from the target and enters detection optics (not shown) at the upper right portion of diagram, while the incoming beam of branch B travels from a source SB at the bottom right, reflects from the target and enters detection optics at the upper left portion of the diagram.

Providing two independent scatterometer branches and placing them at right angles to one another, and at 45° to the target grating enables enhanced functionality as will now be explained. Firstly, by measuring the same target grating from two different directions, measurement results from the branches A and B can be compared in various ways. In one example measurement process, the two branches are used with different polarizations of incoming radiation, which avoids the need to switch polarizations to obtain measurement of a target a different polarizations. Throughput of the instrument can be greatly increased, because switching polarization generally requires a mechanical change within the instrument, with associated delay and settling time. In another application, with the same polarization is used in both branches, the zero order spectra of the target grating taken from different directions can be compared to obtain information on the asymmetry of the grating structure. This can be used for example to measure overlay error of structures fabricated at the resolution limit of the lithographic cell. These are just two examples of the increased functionality provided by the two spectroscopic scatterometers working in parallel as branch A branch B.

In addition to the functionality just described, provision of one or two spectroscopic scatterometers whose zero order path is at an angle to the lines of the target grating 102 enables higher order scatterometry spectra from the target to be detected at a location which is outside the plane of the zero order path. Referring again to FIG. 12, incident radiation from branch A arrives generally in the direction shown by arrow A', while the zero order radiation enters the detection optics of branch A in the direction shown by arrow $A^0$. First order diffracted radiation from the target leaves at an angle indicated by dotted arrow $A^{-1}$, according to a well-known principle of "conical diffraction". Similarly, zero order and first order diffracted radiation for branch B is following the direction indicated by arrows $B^0$ and $B^{+1}$, respectively.

Referring again also to the general layout indicated in FIG. 4, it will be appreciated that the first order detection optics 120 for each branch of the scatterometer are located so as to intercept the beams following the directions $A^{-1}$ and $B^{+1}$. Moreover, as will now be illustrated with reference to FIG. 13, the proximity of the first order beams from both the A and B branches allows the detection optics for the first orders of both branches to be combined using shared components.

Figure 13A:
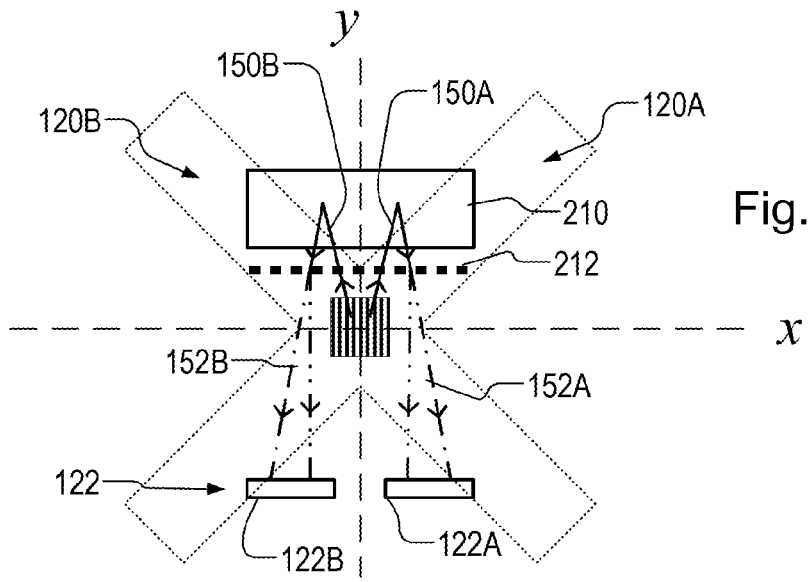
FIGS. 13(a) to 13(d) illustrate the collection of higher order diffracted radiation in the dual-branch scatterometer shown in FIG. 12.
Figure 13B:
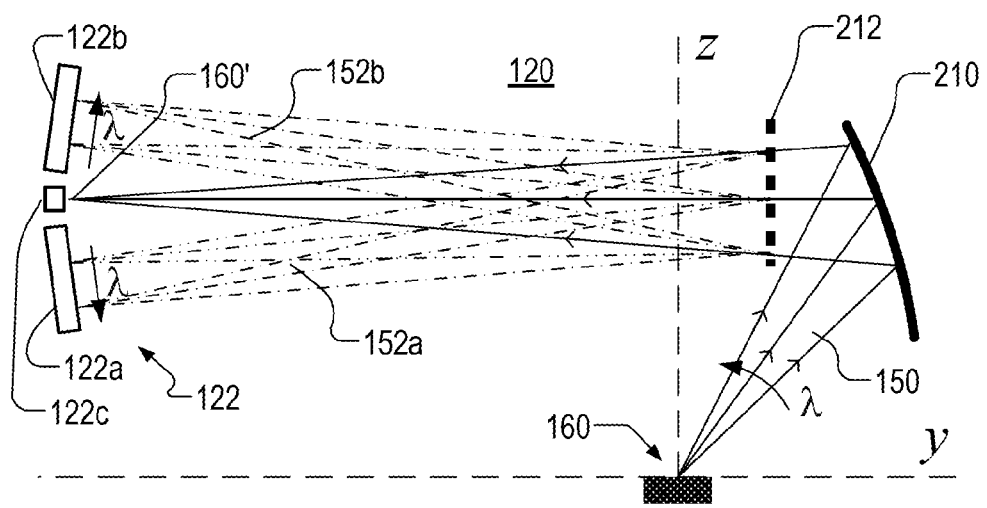

FIG. 13(a) is a schematic plan view of the first order detection optics 120 in the instrument just described, while FIG. 13(b) is a schematic side view of the same detection optics, looking along the X axis. Each view (a) and (b) is only partial, for reasons of clarity. Suffix 'A' or 'B' indicates a component belonging to the first order detection optics of branch A or branch B. Where the suffix is absent, the view is generic to both branches. Suffix 'a' or 'b' indicates components associated with one of two opposite spectra, similar to the use of suffix a or b in FIGS. 4 to 6. Again, where the suffix a or b is absent in this text and/or in the drawing, the feature is generic to both spectra. A first component of the first order detection optics 120 is an elliptical mirror segment 210 this collects first order diffracted beams 150A and 150B from both the A and B branches of the instrument, and focuses them in the direction of detector 122. In the path of each of these beams, a further diffraction grating to 212 is provided to spread the first order beam into a spectrum, the spectrum for each branch A and B being labeled 152A and 152B, respectively.

It will be appreciated by the reader that radiation in the first order diffracted beam 150 is itself a spectrum, spread according to the relationship between a pitch of the target grating and a wavelength λ of the illumination. Following three rays of different wavelengths as drawn, it will be seen that each passes through grating 212 at a different place. Now, taking the spectrum of a spectrum does not provide a better spectrum. However, the design of the first order detection optics is such that the spectroscopic effect due to the target grating itself is cancelled out, by the time the rays reach the detector 122. This is simply achieved by ensuring that, but for the presence of the spectroscopy grating 212, mirror 210 would focus all the first order radiation from spot 160 on the target, to a spot image 160' in the plane of detector 122. Accordingly, when grating 212 spreads the radiation into a pair of spectra 152a and 152b, detectors 122a and 122b receive spectra determined only by the spectroscopic effect of grating 212, and independent of the spectroscopic effect of the target grating. There is therefore no need to focus the first order radiation into a point first, and then feed it to a separate spectrometer.

As in the case of the zero order branch, the grating can be made transmissive or reflective, and can be a phase grating or amplitude grating. In the case of a reflective grating, the spectroscopy grating can be made for example on the surface of the elliptical mirror 210. (The geometry of the lines would in that case be a distorted version of that shown in FIG. 13(c), but this can be calculated and formed by for example photolithographic techniques.)

As seen in the side view, the 'plane' of detector 122 can be made approximately curved, to compensate for aberration in the focus of the different parts of the spectra 152a and 152b. This aberration is exactly the same as that described above, with reference to FIGS. 8 to 10, for the zero order detection optics. As before, the resultant blurring of the spectra can be simply modeled and corrected, if desired, by signal processing.

Figure 13C:
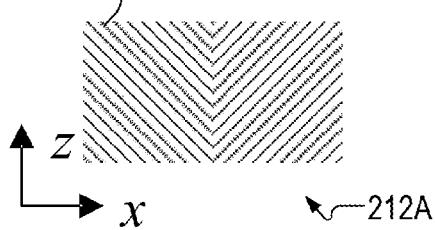
Figure 13D:
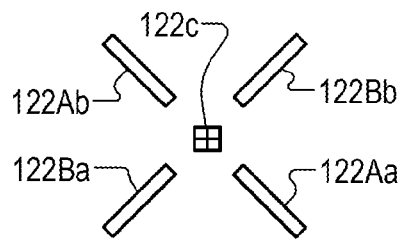

As shown in FIG. 13(c), first order spectroscopy grating 212 has lines arranged at 45°, similar to the zero order grating illustrated in FIG. 7(a). Separate grating portions 212A and 212B are provided for the rays from the two branches A and B, with opposite 45° orientations. FIG. 13(d) illustrates a set of four detectors 122Aa, 122Ab, 122Ba, 122Bb which collect the symmetrical spectra of the first order radiation for the branches A and B, in a manner similar to the operation of the zero order detection optics, described above with reference to FIGS. 7 to 10. A central detector 122c is optional, but could be arranged for example to measure the intensity of the zero order of the first order beam, and/or to provide an independent focus signal for the first order detection optics. Independent focusing of the higher order detection optics is likely to be an unnecessary complication in practice, as the first order detection optics can be designed and manufactured to have the same focal point as the zero order detection optics. In this completely symmetrical arrangement, the central detector 122c, if provided, would receive beams from both branches A and B, however, and this would need to be taken into account in the design and operation of such a detector.

Because the grating 212 used to form the higher order spectrum is distinct from the target grating, its performance can be designed to achieve a desired spectral resolution, and one which is independent of the target grating pitch. This is in contrast to the known MOXIE proposal, in which the target grating is relied upon to perform the spectroscopy.

In conclusion, a spectroscopic scatterometer apparatus has been described with many distinctive and useful features. In addition to analyzing a spectrum of zero order radiation reflected from target, first order diffracted radiation is also captured and its spectrum is analyzed separately. Results of these analyses are combined by numerical processing, to obtain measurements of various properties of the target. In obtaining the spectra from the zero order and/or higher order radiation, a novel spectrometer design based on a simple phase grating can be implemented, in which two symmetrical spectra are detected and combined to obtain a measured spectrum. The combined spectrum is relatively insensitive to focus variations, while a zero order beam through the phase grating can be used directly as a focus sensor.

Other particular features of the examples described bring benefits in the implementation and/or performance of the instrument. For example, placing a spectroscopy grating at an angle to the polarization of the radiation being analyzed allows a spectrum to be obtained without crosstalk between ordinary and extraordinary rays. As another example, placing and optical path of the instrument in a plane which is at an angle to an orientation of the target grating 102, higher order diffracted radiation becomes diverted out of that plane, when it may be more easily captured by higher order detection optics. By providing orthogonal branches of the scatterometer, multiple measurements of the same target grating can be made simultaneously. For example, these may be made with different polarizations, or they may be made with the same polarization, to obtain information on asymmetry of the target grating. In practice, these techniques can be combined and each target to obtain a full set of measurements. For each polarization of incident radiation, the analyzing polarizer P2 can be rotated to 2 different orientations, giving a total of four measurements to discover the polarization-dependence of the scattered spectrum.

Higher order spectra from multiple branches of the instrument can be collected and processed to add to the spectrum information available for reconstruction. With careful design, optical components can be shared between the higher order detection optics of the different branches. First order and higher order diffracted spectra can be obtained. In principle, an analyzing polarizer could be included in the higher order beam prior to the detector 122, similar to polarizer P2 in the zero order branch. However, the lack of a polarizer makes the optics simpler. In the first order branch the light is already dispersed in different angles by the metrology target. As a result, the angular divergence of the light is significantly larger as in the case of the zero order branch. This restricts the types of polarizer that could be used. In the UV waveband there are currently no polarizers that can deal with such diverging light beams.

Referring to the measurement of asymmetry in the target grating, this can be extended to a measurement of overlay error, provided that materials between the two layers whose overlay is being measured are sufficiently transparent to the radiation being used.

The above and numerous other applications of the apparatus will be apparent to the skilled reader and the present invention is not limited to application in any particular measurement. Numerous modifications and variations of the apparatus can be envisaged within the competence of the skilled person. As has been mentioned already, for example, embodiments of the present invention may collect diffracted radiation of orders higher than the first order, and obtained spectra for such radiation to be processed in a reconstruction or other metrology task. While the arrangement having two identical scatterometers arranged at right angles to one another provides particular versatility, it is not essential that these scatterometers are identical, if one would prefer them to have different capabilities. It is not essential, for example, that they both have higher-order branches. Where the two scatterometers do have higher-order branches, it is not necessary for them to share components such as the elliptical mirror 210, if another arrangement would be more practical or provide higher performance. Where a certain number of optical components such as the mirrors M1 to M5 and the elliptical mirror section 210 have been illustrative, optical systems having a greater or fewer number of elements can of course be designed. For example, although it is not believed necessary to achieve a good performance in the currently-intended applications, the blurring of the spectrum due to aberration could be reduced by a more sophisticated detection optics. The skilled reader will appreciate that a trade-off exists, as always, between improving performance in some respects, and introducing degraded performance and/or increased cost by seeking a more sophisticated arrangement.

Figure 14:
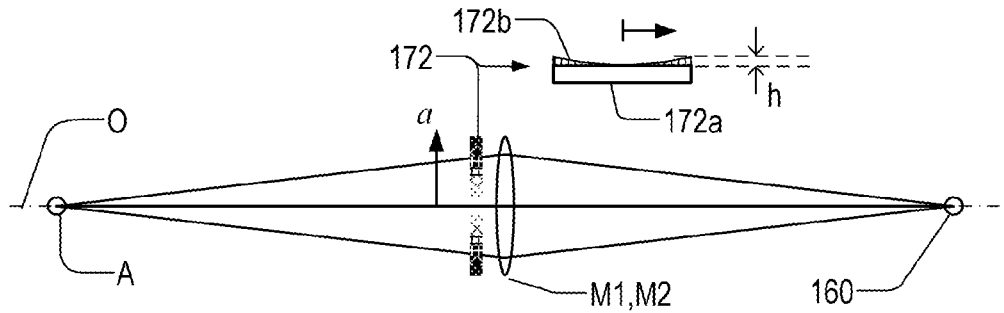
FIG. 14 shows in more detail the form of a filter in the scatterometer for mitigating product cross-talk in the scatterometers of FIGS. 3 to 12, in accordance with the third aspect of the invention.

FIG. 14 illustrates in more detail a filter included in the illumination optics that produces the spot by imaging a source. In the apparatus of FIG. 5, for example, the filter is the filter 172, the source is represented by aperture A. The illumination optics includes focusing elements illustrated as a lens but implemented in this example in the form of mirror M1. The focused illumination spot is labeled 160. In spectroscopic scatterometry it is advantageous if all the measurement light is projected inside the metrology target (in other words: the spot should to "underfill" the grating). Any stray light outside the metrology target can potentially lead to metrology errors, particularly if product features or other targets are present in those areas.

Without the filter 172, diffraction means that the point spread function $I_{PSF}$ of the optics that images the illumination spot on the wafer is a rotationally symmetric Airy function:

$$I_{PSF}(r) = \left[\frac{2J_1(r)}{r}\right]^2$$

Here $J_1$ is a Bessel function and r is a normalized radial coordinate given by:

$$r = a\frac{\pi \times NA}{\lambda}$$

In this expression, NA is the numerical aperture of the imaging optics and $\lambda$ is the wavelength of the light and a is the radius from the center of the Airy function. Each point of light in the source aperture A will be spread in accordance with this function. Even in a case where the aperture is made very small to obtain a small illumination spot, the spot will be spread by diffraction to have sidelobes in accordance with this Airy function. The point spread function in turn dictates the spatial frequency response of the illumination optics, represented by the modulation transfer function MTF.

The Airy function has a central peak and relatively strong oscillatory sidelobes that decay only slowly as a function of radius. The relatively strong and slow decay of the sidelobes result in a relatively large amount of the light this imaged outside the metrology target. This is particularly significant in spectroscopic instruments, where a low illumination NA is generally used.

As shown in FIG. 14, filter 172 has a transmission that decreases with distance a from the optical axis O. We shall refer to it as a radial transmission filter. As shown in the inset detail, filter 172 may be made for example of a metal-coated thin plate 172a with a metal layer 172b of radially increasing thickness h. Example parameters of a filter suitable for UV wavelengths are given below. While the filter is shown as a separate component in this example, it can also be integrated with another element, for example by applying the coating to the mirror M1.

The filter is placed in or near a pupil plane of the illumination optics, so that its effect is to gradually attenuate higher spatial frequencies. This results in a reduction of the sidelobes of the point spread function $I_{PSF}$. Analogous behavior is well-known from signal processing theory where filters are used to reduce "ringing". It is applied here in scatterometry to minimize the amount of the light that leaks outside the metrology target.

In general, any gradual decrease in transmission will give a reduction in sidelobes. However, specific radial variations will give a very efficient reduction. A well-known example from signal theory is the Hanning window function which gives a transmission function T(a) defined by:

$$T(a) = \frac{1}{2}\left[1 + \cos\left(\pi\frac{a}{a_{MAX}}\right)\right]$$

where a is the radial coordinate as shown in FIG. 14 above.

Figure 15A:
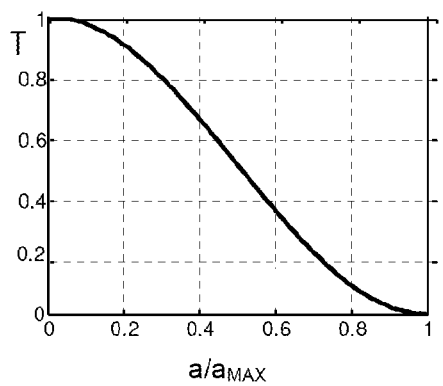
FIGS. 15(a) to 15(d) comprise graphs illustrating various parameters of the filter of FIG. 14 and its effect on a point spread function of the scatterometer.
Figure 15B:
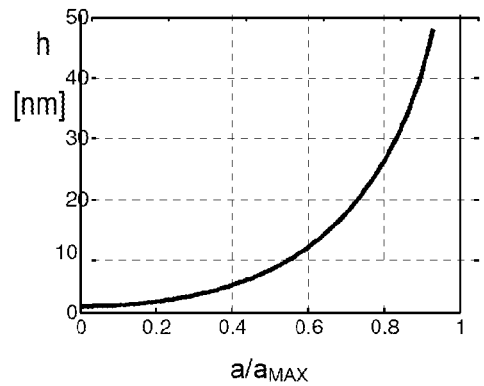

FIG. 15(a) shows the shape of this Hanning window. As already mentioned, this transmission function can be realized in a practical filter by depositing a metal film on a substrate with a radially varying thickness. This thickness distribution shown in FIG. 15(b) can, for example, be made by first depositing a 50 nm thick Ti film on a substrate. This film is then radially etched away by gradually closing a circular diaphragm in an etch chamber. In that case the center has the longest etching time so the Ti film is completely removed. The edge has the shortest etch time so the thickness is not reduced at the edge. Other fabrication methods are, however, also possible. In the example of FIG. 15(b), the metal thickness increases slowly at first and then at an increasing rate with increasing distance a from the center, with the aim that a radial transmission function of the filter approximates the Hanning function.

Figure 15C:
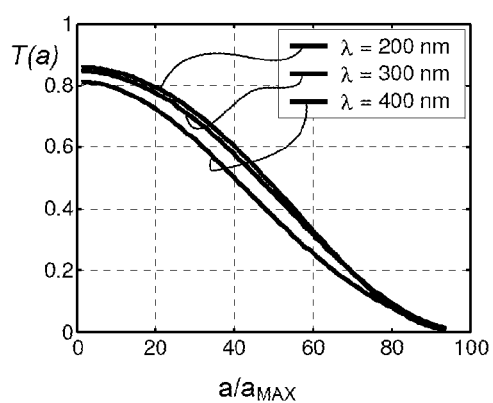

FIG. 15(c) shows the calculated radial transmission function T for three different wavelengths for the thickness distribution shown in FIG. 15(b). T in this notation represents the transmitted intensity (i.e. power), expressed as a fraction of the incident intensity. As can be seen there is some variation in attenuation for the different wavelengths. If necessary, the wavelength variation can be further reduced by mixing several materials or by depositing several films. This, however, increases complexity and may not be needed in practice.

Figure 15D:
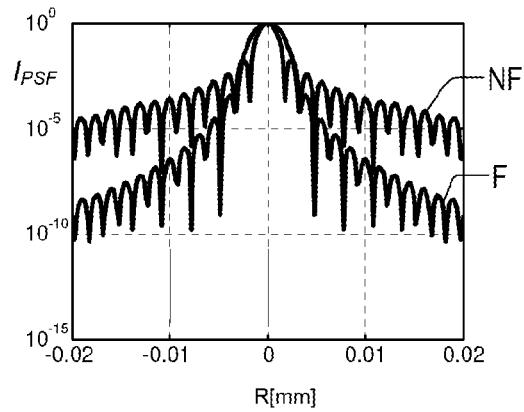

FIG. 15(d) is a graph of the calculated PSF of the illumination optics M1, M2 without (NF) and with (F) the radial transmission filter 172. These functions have been calculated for radiation of $\lambda$=300 nm and focused with an NA=0.1 on a substrate with 60° angle of incidence. (The oblique angle of incidence gives the spot an elliptical shape, and the graphs show the cross-section of the spot on its minor axis). Bearing in mind the vertical log scale, we clearly see that the radial transmission filter will give a very significant reduction of the diffraction rings.

A drawback of the filter is the loss of light, which would lead to increased noise or longer measurement acquisition times. However, the effective NA is also reduced so one could increase the NA of the focusing optics to a level where the effective NA is again almost equal to the originally desired NA. In this way the light loss is probably limited to acceptable levels.

FIGS. 16 and 17 illustrate the phenomenon of apparent surface depression or ASD, and the manner in which it may be measured using the symmetrical spectra detected in the spectroscopic scatterometer apparatuses described herein.

In lithography using an apparatus such as that shown in FIG. 1, the wafer height is optically measured with a level sensor. The operation of this level sensor typically is based on optical triangulation. A pattern is projected on the wafer at an oblique angle and this reflected pattern is re-imaged on a detector. A height variation on the wafer will result in the shift of the pattern on the detector. This is results in a measured height variation. The height variations are mapped across the substrate W prior to exposing the substrate to the patterned beam using projection system PS. Errors in height measurement leads to poor focusing of the desired product pattern and therefore limit the performance of the lithography step as a whole.

FIG. 16(a) shows a typical substrate W undergoing level sensing. An underlying Si substrate 1600 is coated with radiation sensitive resist 1602, with an intermediate anti-reflection layer 1604. The layer thicknesses are not shown to scale. It will be appreciated that in the majority of lithographic steps, other layers previously applied and perhaps patterned may lie between layer 1604 and the ultimate substrate 1600. Incoming radiation from the level sensor is shown at 1606 and reflected rays are shown at 1608. Ideally, the sensor should measure the top of the resist surface. Typically the known level sensors works with visible light and resist and BARC layers are transparent for the measurement light. Moreover, layers that may lie beneath the BARC layer are also transparent for the measurement. As a result, the measurement light penetrates the stack of resist and process layers, resulting in the illustrated measurement error which is called the Apparent Surface Depression or ASD. In practice this ASD effect can become very large (>100 nm).

The real problem, however, is not so much the magnitude of this error but the fact that it can vary from wafer-to-wafer and from lot-to-lot. Therefore it cannot be corrected without information specific to each wafer, which is costly in terms of throughput. As a first step to address to reduce these variations a level sensor in future may use UV instead of visible light. In case of the UV LS the measurement light is absorbed in the top layers of the stack so the resulting process sensitivity due to stack variations will be significantly reduced. However, the ASD will still be a problem for the UV level sensor for a few types of process layer that are partially transparent even in the UV range. In practice, it is not always possible to predict beforehand whether the UV level sensor will be sufficiently effective, or if leveling problems are still due to residual ASD variations. In order to assess if leveling problems are due to residual ASD variations it is desirable if a measurement system were available that could detect variations in the LS process dependency.

It may be noticed that the oblique incidence and reflection of the rays 1606 and 1608 in FIG. 16(a) is similar to the oblique incidence and reflection of illumination and diffracted rays 142, 144 in the scatterometer of FIG. 5. The inventor has recognized that the novel spectroscopic scatterometer disclosed herein can be used instead or in addition to detect residual ASD variations. This information can optionally be used to derive a correction signal that can be fed forward to the leveling system.

FIG. 16(b) illustrates a reflectance spectrum of a target substrate measured by the scatterometer. The reflectance R is simply the intensity $I_R$ of the detected radiation, divided by the intensity $I_0$ of the incident radiation. All three quantities these vary as a function of wavelength $\lambda$. As already described in relation to FIG. 7, it needs to be taken into account that the sensitivity of the detector varies with wavelength also. The apparent surface depression ASD is also a function of wavelength, and FIG. 16(c) shows the calculated ASD for a typical stack.

Referring to FIG. 17, we see again the detector layout of the spectroscopic scatterometer that can be used to measure process-dependency effects of the level sensor in a lithographic system. The symmetrical spectra are shown in graphs above each detector. The spectra in this figure have been converted already to reflectance $R_a$ and $R_b$, while the spectra in FIG. 10 were shown in their intensity values $I_a$ and $I_b$. The exact operation of this scatterometer in various embodiments has already been discussed above in relation to FIGS. 4 to 13 and will not be repeated in too much detail here. In principle, however, what we describe here is an independent instrument for obtaining information about ASD. The fact that the same hardware also forms the basis of a spectroscopic scatterometer capable of many other measurements is something that the designer and user of the apparatus may exploit or ignore as they wish.

Recalling FIGS. 4 and 5, the aperture A is imaged on the substrate W via mirror M1. The second mirror M2 is used to image the measurement spot 160 onto detector arrays 110a and 110b and the focus sensor 110c. Because of phase grating G, the signal measured on detectors 110a 110b is the wavelength spectrum of the reflected light. Since we illuminate the target at an oblique angle, the location of the spectrum on the detectors D1 and D2 is very sensitive to wafer height errors. As described already above, we monitor and control the wafer height very accurately with the focus sensor 110c and focus actuator 170. The measured wafer height, however, is wavelength dependent. This wavelength-dependency we can measure using the symmetrical spectra obtained by detector arrays 110a, 110b.

Referring now to FIGS. 16 and 17 together, the phenomenon of ASD means that the reflected spot in the scatterometer, as measured by focus sensor 110c, lies beneath the true position of the top of the resist-air interface. However the ASD effect varies in magnitude with the wavelength. As a result of this, the spectra on the detector arrays 110a and 110b will show a small but significant wavelength-dependent shift as indicated by the small arrows on the spectra of FIG. 17. In the x-coordinate system, this shift has the same direction. By contrast, the wavelength ($\lambda$) coordinate on the two detector arrays 110a and 110b, points in opposite directions. As a result, the direction of the ASD-induced shift of the spectrum is opposite on detectors 110a and 110b, and in their spectra $R_a$ and $R_b$.

This symmetry effect was exploited above to obtain a spectrum using the average of the two spectra, making the spectrum less sensitive to focus errors. The inventor has recognized that the same symmetry effect enables us to obtain information about the ASD effect at a given location on a substrate using the difference of the two spectra. Recall that the two spectra should be identical, and that a general focus error results in a complete shift of the spectra as illustrated in FIG. 10. It can be shown that a difference signal between the detected spectra at each wavelength is related to the wavelength-dependent ASD by the following relationship:

$$\frac{R_a - R_b}{2} \propto \frac{dR}{d\lambda} \times ASD(\lambda)$$

According to this equation, we cannot detect ASD effects in the areas in the spectrum where $dR/d\lambda=0$ so there will be some blank regions in the measured ASD spectrum. It is expected, however, that these areas are limited. If necessary one can interpolate ASD values for these regions, or one could shape the source radiation spectrum to add a gradient to the illumination intensity $I_0(\lambda)$ in regions where $dR/d\lambda=0$. This is likely to be an undesirable complication, however.

The measured ASD information can be used in various ways. The most interesting application area is probably to use this information to further improve the robustness of the level sensor. For example, this method can be used to measure the ASD effect on the wafer before it enters the exposure tool. In any case, the capability to detect ASD variations is a useful feature of the novel spectroscopic scatterometer hardware. It will be understood that the ASD spectrum measurement can be added to the capabilities of the described spectroscopic scatterometer by a simple addition to the software in processor PU (not shown in FIGS. 4 to 13 but provided in each case).

Figure 18:
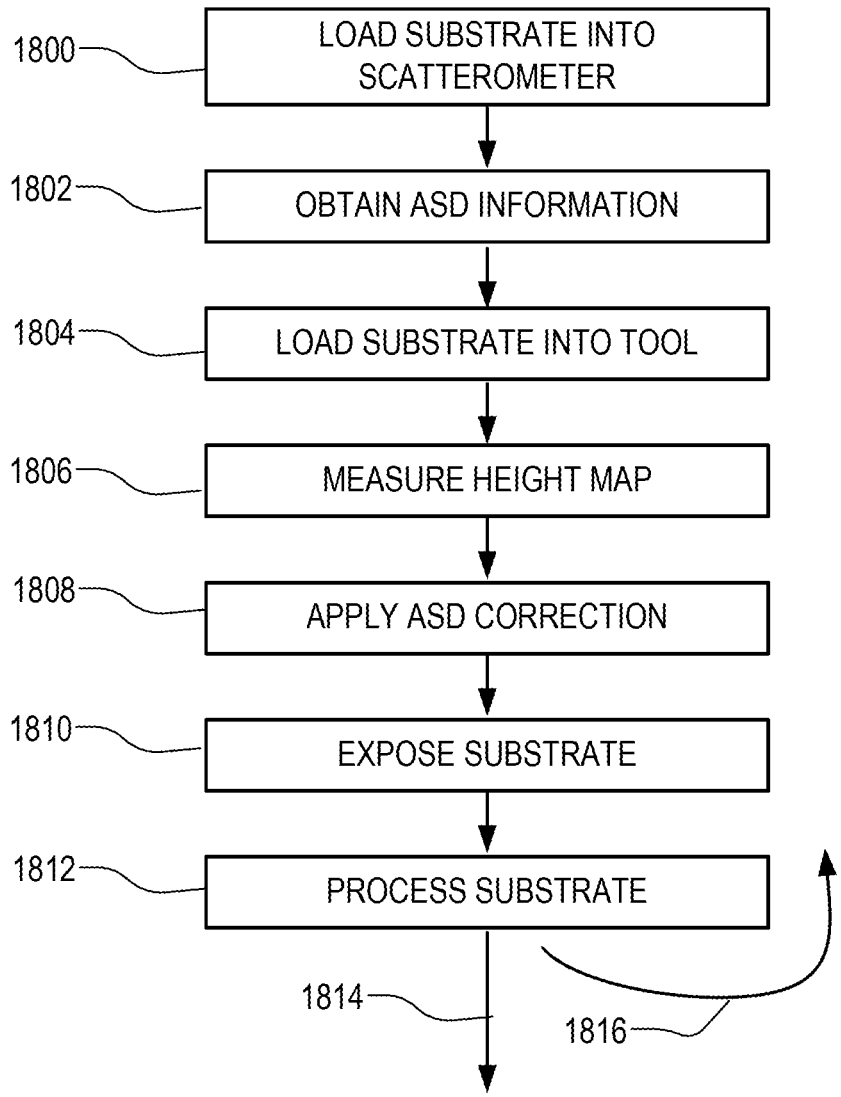
FIG. 18 is a flowchart of a method of patterning substrates according to an embodiment of the invention in its fourth aspect.

FIG. 18 is a flowchart illustrating the application of ASD measurement to improve imaging in a lithographic process. At 1800 the substrate is loaded into a spectroscopic scatterometer, which can be separate from a lithographic tool. The scatterometer is operated (1802) as described above to obtain measurements of ASD at one or more wavelengths, and at one or more positions. Of particular interest is any wavelength or wavelengths used in the level sensor of the lithographic tool. The ASD may be measured for example at inner an outer portions of the substrate, to account for differences in layer thicknesses due to spin coating or process steps like chemical mechanical polishing (CMP). At 1804 the substrate is loaded into the lithographic tool in preparation for a patterning operation. The tool may be of the type shown in FIG. 1 for example. At 1806 the tool uses its level sensors LS to obtain a height map of the substrate surface. At 1808 a correction is applied to the measured height map, based on the ASD information previously obtained using the scatterometer. (The correction could if preferred be programmed into the level sensor while it operates; the result is the same).

At 1810 the substrate is exposed as described in relation to FIG. 1, applying a pattern from patterning device MA by imaging it onto each target portion C of the substrate W. Because the height map used for focusing during this imaging has been corrected to account for ASD effects that are specific to this substrate, the image quality is improved. At 1812 the substrate is processed as described with reference to FIG. 2 above, to develop the pattern exposed in the resist layer. Depending which particular product layer is being patterned, the processing either concludes at 1614 or returns at 1616 for further steps of coating, exposing, etching and so forth.

Further embodiments according to the invention are provided in below numbered clauses:

1. Inspection apparatus comprising a spectroscopic scatterometer having:
   illumination optics for directing broadband radiation with an angle of incidence at a spot on a target structure, the target structure in use comprising a periodic grating;
   zero order detection optics for receiving radiation reflected from the target and for forming and detecting a spectrum of the reflected radiation; and
   higher order detection optics for receiving radiation diffracted at one or more higher orders by the periodic grating in the target structure, and for forming and detecting a spectrum of the received diffracted radiation.

2. Inspection apparatus according to clause 1 wherein the higher order detection optics comprise:
   a focusing arrangement for focusing the higher order diffracted radiation emanating from the spot into an image spot comprising all wavelengths of radiation,
   at least one higher order spectrum detector positioned to at least one side of the image spot, and
   a diffraction grating positioned in an optical path between the spot and the image spot so as to form a spectrum of the higher order diffracted radiation on the higher order spectrum detector.

3. Inspection apparatus according to clause 2 wherein the diffraction grating is symmetrical so as to form a symmetrical pair of spectra of the higher order diffracted radiation, and a pair of spectrum detectors are provided so as to capture both of the pair of spectra, the apparatus further comprising a processor for combining measurements from both detectors to obtain a single detected spectrum.

4. Inspection apparatus according to clause 2 or 3 wherein the diffraction grating comprises a phase grating of either transmissive or reflective type.

5. Inspection apparatus according to clause 2, 3 or 4 wherein the focusing arrangement comprises a single curved mirror.

6. Inspection apparatus according to any preceding clause wherein the illumination optics and zero order detection optics process radiation generally in a first plane perpendicular to a plane the target structure, while the higher order detection optics are arranged to process radiation in a second plane, angled relative to the first plane, the higher order diffracted radiation entering the second plane during use of the apparatus as a result of an oblique orientation of lines the periodic grating in the target structure, relative to the first plane.

7. Inspection apparatus according to clause 6 wherein the first plane is set at an angle of 45° relative to the expected orientation of the lines in the periodic grating.

8. Inspection apparatus according to clause 6 or 7 wherein a second spectroscopic scatterometer is provided for simultaneous measurement of the same target structure, a first plane of the second spectroscopic scatterometer being arranged at right angles to the first plane of the first-mentioned spectroscopic scatterometer.

9. Inspection apparatus according to clause 8 wherein one or more optical components are shared between the higher order detection optics of the first-mentioned and second scatterometers.

10. An inspection apparatus according to any preceding clause arranged for operation with radiation at wavelengths shorter than 400 nm, wherein the illumination optics comprise one or more curved mirrors for focusing the radiation into a spot on the target structure, while the zero and higher order detection optics each comprise one or more curved mirrors for focusing an image of the spot at a point to one side of a spectrum detector.

11. Inspection apparatus comprising a spectroscopic scatterometer having:
    illumination optics for directing broadband radiation with an angle of incidence at a spot on a target structure;
    detection optics for receiving radiation diffracted at a zero or higher order from the target structure and for forming and detecting a spectrum of the diffracted radiation,
    wherein the detection optics comprises a symmetric diffraction grating arranged to form a symmetrical pair of spectra of the reflected radiation, and wherein a pair of spectrum detectors are arranged to detect both of the spectra, the apparatus further comprising a processor for combining measurements from both detectors to obtain a single detected spectrum of the reflected radiation.

12. Inspection apparatus according to clause 11 wherein a further detector is arranged to receive a zero order beam of the grating, the further detector being located at a point generally in between the pair of spectrum detectors, and wherein signals from the further detector are used for monitoring focus of the spot on the target structure.

13. Inspection apparatus according to clause 11 or 12 comprising first and second spectroscopic scatterometers of generally similar form arranged for simultaneous measurement of the same target structure, wherein the illumination optics and detection optics of each scatterometer are arranged to process radiation generally in a first plane perpendicular to a plane of the target structure, and wherein a first plane of the second scatterometer is arranged at an angle to the first plane of the first-mentioned scatterometer.

14. Inspection apparatus according to clause 13 wherein the first planes of the first and second spectroscopic scatterometers are arranged at right angles to one another.

15. Inspection apparatus according to any of clauses 11 to 14 wherein the detection optics is arranged to capture zero order diffracted radiation, being radiation reflected from the target structure, the detection optics including an analyzing polarizer in a path of the reflected radiation prior to the phase grating, the analyzing polarizer comprising a Rochon prism arranged to transmit ordinary and extraordinary rays in different directions thereby to select only one polarization for the formation of the spectra, and wherein the phase grating has lines oriented at an oblique angle relative the selected polarization, whereby radiation of a different polarization will have its spectra formed by the phase grating at a location away from the pair of spectrum detectors.

16. Inspection apparatus according to any of clauses 11 to 15 wherein the detection optics comprise a focusing arrangement for focusing the diffracted radiation emanating from the spot into an image spot at a location generally in between the spectrum detectors, the diffraction grating being positioned in an optical path of the focusing arrangement between the spot and the image spot so as to form the spectra of the diffracted radiation on the spectrum detectors.

17. Inspection apparatus according to clause 16 arranged for operation with radiation at wavelengths shorter than 400 nm, wherein the focusing arrangement comprises one or more curved mirrors.

18. Inspection apparatus according to any of clauses 11 to 17 further comprising means for processing the spectrum to correct for an aberration caused by rays of the reflected radiation being non-parallel at the location of the phase grating.

19. Inspection apparatus according to any of clauses 11 to 18 wherein the diffraction grating is a transmissive phase grating.

20. Inspection apparatus according to any of clauses 11 to 18 wherein the diffraction grating is a reflective phase grating.

21. Inspection apparatus according to clause 20 wherein the diffraction grating is formed on a curved mirror that serves also for focusing the diffracted radiation emanating from the spot into an image spot at a location generally in between the spectrum detectors.

22. A method of measuring properties of a target structure on a substrate, a target structure including a periodic grating, the method comprising obtaining a zero order spectrum and at least one higher order spectrum from the target structure using an inspection apparatus according to any of clauses 1 to 10, and processing the measured spectra so as to obtain measurements of one or more parameters of the target structure.

23. A method according to clause 22 wherein the zero order and higher order spectra are measured for the same target more than once, using different polarizations of incident radiation and/or selecting different polarizations in one or both of the zero order detection optics and higher order detection optics.

24. A method according to clause 22 or 23 wherein the zero order and higher order spectra are measured for the same target using different angles of incidence of radiation relative to an orientation of the periodic grating in the target structure, and wherein measurements obtained from the different angles of incidence, combined to measure an asymmetry property of the target structure.

25. A method according to clause 24 wherein the spectra are measured in parallel using different angles of incidence by providing two spectroscopic scatterometers with different orientations, arranged to be directed at the same target structure.

26. A method of measuring properties of a target structure on a substrate, a target structure including a periodic grating, the method comprising obtaining a spectrum from the target structure using an inspection apparatus according to any of clauses 11 to 21, and processing the detected spectrum so as to obtain measurements of one or more parameters of the target structure.

27. A method according to clause 26 further comprising processing the spectrum to correct for an aberration caused by rays of the reflected radiation being non-parallel at the location of the phase grating.

28. An optical apparatus including illumination optics for focusing a beam of radiation at a spot on a target structure, wherein the illumination optics include a filter provided at or near a pupil plane, the filter imposing on the beam a transmission loss increasing with radial distance from an optical axis of the beam.

29. An apparatus according to clause 28 wherein the filter comprises a transparent substrate having a metallic coating whose thickness increases radially away from a central point.

30. An apparatus according to clause 29 wherein the thickness increases slowly at first and then at an increasing rate with increasing distance from the central point, such that a radial transmission function of the filter approximates a Hanning function.

31. An apparatus according to clause 28, 29 or 30 wherein the illumination optics comprises one or more reflective focusing elements.

32. An apparatus according to clause 28, 29, 30 or 31 further comprising a source of UV radiation to form the beam.

33. A method of measuring properties of a target structure on a substrate, the method comprising illuminating the target structure with a spot of radiation using an optical apparatus according to any of clauses 28 to 32, detecting radiation diffracted by the target structure and processing the detected radiation to obtain measurements of one or more parameters of the target structure.

34. A spectroscopic scatterometer having illumination optics for directing broadband radiation with an angle of incidence at a spot on a target structure, detection optics for receiving radiation diffracted at a zero or higher order from the target structure and for forming and detecting a spectrum of the diffracted radiation, wherein the detection optics comprises a symmetric diffraction grating arranged to form a symmetrical pair of spectra of the reflected radiation, and wherein a pair of spectrum detectors are arranged to detect both of the spectra, the apparatus further comprising a processor for comparing measurements from both detectors to obtain information of an apparent surface depression at the location of the target structure on a substrate.

35. A method of performing a lithographic patterning step by applying a pattern to a substrate using a projection system, wherein focusing of the projection system being based on height measurements made at a plurality of locations across the substrate, and wherein a correction is applied to the height measurements based on information of an apparent surface depression obtained using a spectroscopic scatterometer according to clause 34.

36. A method of manufacturing a device comprising applying one or more device patterns to a substrate by a method according to clause 35 and processing the patterned substrate to form devices in accordance with the applied patterns.

Although specific reference may be made in this text to the use of lithographic apparatus in the manufacture of ICs, it should be understood that the lithographic and metrology apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, and use of the terms "wafer" or "die" herein may be considered as synonymous with the more general terms "substrate" or "target portion", respectively. The substrate referred to herein may be processed, before or exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the present invention in the context of optical lithography, it will be appreciated that the present invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

While the embodiments above have been designed to operate using radiation at UV wavelengths, the designs can be adapted by the skilled person to use a different or wider range of wavelengths, if desired. The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the present invention have been described above, it will be appreciated that the present invention may be practiced otherwise than as described. For example, the present invention, particularly with regard to the control of the measurement process and processing of the results for calibration and reconstruction, may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the present invention as described without departing from the scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the present invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. An inspection apparatus, comprising:
a spectroscopic scatterometer comprising:
illumination optics configured to direct broadband radiation with an angle of incidence at a spot on a target structure, the target structure in use comprising a periodic grating;
zero order detection optics configured to receive radiation reflected from the target and for forming and detecting a spectrum of the reflected radiation; and
higher order detection optics configured to receive radiation diffracted at one or more higher orders by the periodic grating in the target structure, and to form and detect a spectrum of the received diffracted radiation,
wherein the higher order detection optics comprise a diffraction grating that is symmetrical and configured to form a symmetrical pair of spectra of the higher order diffracted radiation,
wherein a pair of spectrum detectors are configured to capture the pair of spectra, and
wherein the diffraction grating is a phase grating comprising lines oriented at an oblique angle relative to a selected polarization, such that radiation of a different polarization will have its spectra formed by the phase grating at a location away from the pair of spectrum detectors.

2. The inspection apparatus of claim 1, wherein the higher order detection optics further comprise:
a focusing arrangement configured to focus the higher order diffracted radiation emanating from the spot into an image spot comprising all wavelengths of radiation, and at least one higher order spectrum detector positioned to at least one side of the image spot, wherein the diffraction grating is positioned in an optical path between the spot and the image spot to form a spectrum of the higher order diffracted radiation on the higher order spectrum detector.

3. The inspection apparatus of claim 2, wherein a processor is configured to combine measurements from both detectors to obtain a single detected spectrum.

4. The inspection apparatus of claim 1, arranged for operation with radiation at wavelengths shorter than 400 nm, wherein:
the illumination optics comprise one or more curved mirrors configured to focus the radiation into a spot on the target structure, and
the zero and higher order detection optics each comprise one or more curved mirrors configured to focus an image of the spot at a point to one side of a spectrum detector.

5. An inspection apparatus including a spectroscopic scatterometer, comprising:
illumination optics configured to direct broadband radiation with an angle of incidence at a spot on a target structure;
detection optics configured to receive radiation diffracted at a zero or higher order from the target structure and to form and detect a spectrum of the diffracted radiation,
wherein the detection optics comprises a symmetric diffraction grating arranged to form a symmetrical pair of spectra of the reflected radiation, and
wherein a pair of spectrum detectors are arranged to detect both of the spectra, and
a processor configured to combine measurements from both detectors to obtain a single detected spectrum of the reflected radiation,
wherein the symmetric diffraction grating comprises a phase grating comprising lines oriented at an oblique angle relative to a selected polarization, such that radiation of a different polarization will have its spectra formed by the phase grating at a location away from the pair of spectrum detectors.

6. The inspection apparatus of claim 5, wherein a further detector is arranged to receive a zero order beam of the grating, the further detector being located at a point in between the pair of spectrum detectors, and wherein signals from the further detector are used for monitoring focus of the spot on the target structure.

7. The inspection apparatus of claim 5, comprising:
first and second spectroscopic scatterometers arranged for simultaneous measurement of the same target structure,
wherein the illumination optics and detection optics of each scatterometer are arranged to process radiation in a first plane perpendicular to a plane of the target structure, and
wherein a first plane of the second scatterometer is arranged at an angle to the first plane of the first-mentioned scatterometer.

8. The inspection apparatus of claim 5, wherein:
the detection optics is arranged to capture zero order diffracted radiation, being radiation reflected from the target structure,
the detection optics include an analyzing polarizer in a path of the reflected radiation prior to the phase grating,
the analyzing polarizer comprises a Rochon prism arranged to transmit ordinary and extraordinary rays in different directions thereby to select only one polarization for the formation of the spectra.

9. The inspection apparatus of claim 5, wherein:
the detection optics comprise a focusing arrangement configured to focus the diffracted radiation emanating from the spot into an image spot at a location in between the spectrum detectors, and
the diffraction grating is positioned in an optical path of the focusing arrangement between the spot and the image spot so as to form the spectra of the diffracted radiation on the spectrum detectors.

10. The inspection apparatus of claim 9 arranged for operation with radiation at wavelengths shorter than 400 nm, wherein the focusing arrangement comprises one or more curved mirrors.

11. The inspection apparatus of claim 5, further comprising a processor for processing the spectrum to correct for an aberration caused by rays of the reflected radiation being non-parallel at the location of the phase grating.

12. A spectroscopic scatterometer, comprising:
illumination optics configured to direct broadband radiation with an angle of incidence at a spot on a target structure,
detection optics configured to receive radiation diffracted at a zero or higher order from the target structure and for forming and detecting a spectrum of the diffracted radiation,
wherein the detection optics comprises a symmetric diffraction grating arranged to form a symmetrical pair of spectra of the reflected radiation, and
wherein a pair of spectrum detectors are arranged to detect both of the spectra, and
a processor configured to compare measurements from both detectors to obtain information of an apparent surface depression at the location of the target structure on a substrate,
wherein the symmetric diffraction grating is a phase grating comprising lines oriented at an oblique angle relative to a selected polarization, whereby radiation of a different polarization will have its spectra formed by the phase grating at a location away from the pair of spectrum detectors.

* * * * *